US 6,736,797 B1

(12) United States Patent
Larsen et al.

(10) Patent No.: US 6,736,797 B1
(45) Date of Patent: *May 18, 2004

(54) SUBCUTANEOUS INFUSION SET

(75) Inventors: Bjørn Gullak Larsen, Roskilde (DK);
Orla Mathiasen, Roskilde (DK); Lars Bjarne Frederiksen, Roskilde (DK);
Marc Delzac, Roskilde (DK); Claude Teissen-Simony, Roskilde (DK)

(73) Assignee: Unomedical A/S, Lynge (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/446,448

(22) PCT Filed: Jun. 19, 1998

(86) PCT No.: PCT/DK98/00262
§ 371 (c)(1),
(2), (4) Date: May 16, 2000

(87) PCT Pub. No.: WO98/58693
PCT Pub. Date: Dec. 30, 1998

(51) Int. Cl.[7] ............... A61M 5/178; A61M 25/00
(52) U.S. Cl. .................. 604/167.05; 604/533
(58) Field of Search ............... 604/27, 32, 167.01, 604/167.03, 167.05, 246, 248, 533–535, 537–539, 288.02; 137/625.41, 625.46, 625.47; 251/208, 304, 309, 310

(56) References Cited

U.S. PATENT DOCUMENTS

| | | |
|---|---|---|
| 1,155,271 A | 9/1915 | Philips |
| 1,188,180 A | 6/1916 | Kells |
| 2,001,638 A | 5/1935 | Tornsjo |
| 2,898,917 A | 8/1959 | Wallace |
| 3,253,594 A | 5/1966 | Matthews et al. |
| 3,310,051 A | 3/1967 | Schulte |
| 3,487,837 A | 1/1970 | Petersen |
| 3,783,868 A | 1/1974 | Bokros |
| 3,896,810 A | 7/1975 | Akiyama |
| 4,153,058 A | 5/1979 | Nehme |
| 4,318,401 A | 3/1982 | Zimmerman |
| 4,392,853 A | 7/1983 | Muto |
| 4,393,873 A | 7/1983 | Nawash et al. |
| 4,412,834 A | * 11/1983 | Kulin et al. .............. 604/29 |
| 4,419,094 A | 12/1983 | Patel |
| 4,464,178 A | 8/1984 | Dalton |
| 4,488,877 A | 12/1984 | Klein et al. |
| 4,552,561 A | 11/1985 | Eckenhoff et al. |
| 4,583,977 A | 4/1986 | Shishov et al. |
| 4,619,652 A | 10/1986 | Eckenhoff et al. |
| 4,632,671 A | 12/1986 | Dalton |

(List continued on next page.)

FOREIGN PATENT DOCUMENTS

| | | |
|---|---|---|
| EP | 0 157 906 A1 | 5/1982 |
| EP | 0 133 520 A2 | 11/1983 |
| EP | 0 239 244 A1 | 9/1987 |
| GB | 1240312 | 10/1968 |

*Primary Examiner*—Michael J. Hayes
(74) *Attorney, Agent, or Firm*—Brinks Hofer Gilson & Lione

(57) ABSTRACT

A subcutaneous infusion set for administering a medication or a therapeutic fluid to a patient is disclosed. The infusion set includes a base element having a cavity and an entry lumen. A closing element is mounted on the base element to be rotatable about an axis through the base element and having an aperture, which in one position of the closing element in relation to the base element is aligned with the entry lumen of the base element and in a further rotated position of the closing element in relation to the base element, the closing element covers the entry lumen the base element. A cannula is mounted in and extends from the base element, the cannula having a lumen therethrough, the lumen communicating with the entry lumen through the cavity. Connector means for administering a fluid to the entry lumen are provided.

18 Claims, 27 Drawing Sheets

U.S. PATENT DOCUMENTS

| | | |
|---|---|---|
| 4,675,006 A | 6/1987 | Hrushesky |
| 4,710,176 A | 12/1987 | Quick |
| 4,734,092 A | 3/1988 | Millerd |
| 4,755,173 A | 7/1988 | Konopka et al. |
| RE32,922 E | 5/1989 | Levin et al. |
| 4,867,745 A | 9/1989 | Patel |
| 4,966,588 A | 10/1990 | Rayman et al. |
| 5,176,662 A | 1/1993 | Bartholomew et al. |
| 5,207,641 A * | 5/1993 | Allton .................. 604/32 |
| 5,522,803 A | 6/1996 | Teissen-Simony |
| 5,545,143 A | 8/1996 | Fischell |
| 5,968,011 A | 10/1999 | Larsen et al. |
| 6,017,328 A | 1/2000 | Fischell et al. |

\* cited by examiner

SUBCUTANEOUS INFUSION SET

BACKGROUND OF THE INVENTION

The present invention relates to infusion devices for subcutaneous delivery of a medication or a therapeutic fluid by means of an external infusion system and more particularly to an infusion device having releasably connected means for delivery of the medication or the therapeutic fluid from the external infusion system.

Infusion devices are generally known in the art for delivering a medication or a therapeutic fluid to a subcutaneous site in a patient. Such devices commonly comprise a tubular cannula extending from a housing adapted to receive the desired medication via disconnectable means for suitable connection to further components of the infusion system. The possibility of disconnecting the infusion set from the further parts of the infusion system is provided in order to improve the user comfort. The user is enabled to perform activities which do not allow the presence of a pump or the like, or which are hindered by the presence of a pump or the like. In the disconnected state only a part of the infusion set is worn by the patient. This allows for increased mobility. In order to provide such disconnectable means and still maintain a fluid-tight sealing towards the interior of the housing and the tubular cannula that prevents contamination of the infusion site, such devices are commonly provided with a self-sealing penetrable septum on either the housing or the disconnectable part and a hollow needle on the other part adapted to penetrate the septum. Upon withdrawal of the needle from the septum this provides a fluid-tight sealing towards the interior of the housing. The septum and the needle further provide a fluid-tight sealing between the housing and the connector means when medication or therapeutic fluid is delivered to the patient from the external infusion system. Subcutaneous infusion devices of this generally known type are known from e.g. U.S. Pat. No. 5,522,803 to Teissen-Simony and U.S. Pat. No. 5,545,143 to Fischell.

The manufacture of such device including a septum and a needle is rather cumbersome. Further the use of a septum and a needle may lead to some disadvantages during use of such device, viz. a so-called coring whereby, upon penetration of the septum, the hollow needle may become clogged by material from the septum, which may be harmful to the patient since the medication or the therapeutic fluid cannot be delivered as expected, and the potential danger of unintended needle sticks.

For these reasons there is a need for improvements in the infusion devices of the type mentioned in the foregoing, and particularly with respect to providing an infusion device which is far less cumbersome from a manufacturing point of view and which is not clogged by material from a septum and with respect to a device which does not need a septum and a needle to provide a fluid-tight sealing between housing and connector means in a mutually mounted position for these elements. The infusion device according to the invention remedies the above mentioned disadvantages and provides further advantages which will become apparent from the following description.

SUMMARY OF THE INVENTION

The advantages of the present invention are obtained by means of an infusion device comprising:
- a base element having a cavity and an entry lumen;
- a cannula mounted in and extending from said base element, said cannula having a lumen therethrough, said lumen communicating with the entry lumen through said cavity;
- connector means for administering a fluid to said entry lumen;
- a closing element mounted on said base element to be rotatable about an axis through said base element and having an aperture, where the aperture in one position of the closing element in relation to the base element is aligned with said entry lumen of said base element and in a further rotated position of the closing element in relation to the base element the closing element covers said entry lumen in said base element.

By means of the base element and the closing element which, upon mutual rotation of the closing element and the base element, enables a covering of the lumen in the hub, the need for a self-sealing septum for shutting off the opening in the infusion device where the medication is delivered has become eliminated. Since there is no longer a need for a septum, a needle on the means for delivering the medication or the therapeutic fluid can also be omitted. This means that the manufacturing process has been significantly simplified and production costs have been decreased. The need for the elements causing the coring has been eliminated, whereby the coring problem has likewise been eliminated. The danger of unintended needle sticks is precluded.

In a preferred embodiment the base element comprises a hub with a top and a bottom and an outer surface extending between said top and said bottom, wherein the cavity is formed within said cavity and said entry lumen extend between said outer surface and said cavity and wherein the closing element has substantially the form of a ring element. Hereby a reliable and easy placing of the connector is obtained.

In a preferred embodiment of the invention the closing element of the infusion set further comprises a flange having an inwardly facing surface directed towards the central axis of said hub and wherein said means for administering fluid to said opening in said flange comprises an outward facing surface directed away from central axis of said hub, said outwardly facing surface matching said inward facing surface of said flange of said closing element upon rotation of said closing element in relation to said base element. Hereby it is possible to releasably lock the connector means for administering the medication or the therapeutic fluid in relation to the base element and the closing element. A corresponding effect could be realised if said connector means is secured in relation to said base element and said flange in the area around the aperture is provided with an increased outer diameter hereby providing a pressure against said connector means upon rotation of said closing element.

In a further convenient embodiment the inwardly facing surface, the outwardly facing surface or both surfaces has/have a curvature urging the connector means for administering medication towards the inner flange of the closing element upon rotation of the closing element in relation to the base element. Hereby it is possible to obtain sufficient sealing between the connecting element of the connector means for administering the medication or the therapeutic fluid and the flange without any further sealing means. This desired effect can be obtained by means of an off-set axis of rotation.

It is however a possibility that further sealing means are provided between the hub and the flange and/or between the flange and the means for delivering medication, in order to prevent leakage between these elements. Such sealing means are preferably O-rings or the like.

In a further preferred embodiment the subcutaneous infusion set further comprises means for releasably interlocking the base element and the closing element in relation to a mutual rotation about said central axis. Hereby it is ensured that the possibility of unintended rotation of the closing element in relation to the base element is eliminated, which could otherwise result in a blocking of the administering of the medication or the therapeutic fluid during use.

In a further preferred embodiment of the subcutaneous infusion set means are provided for preventing rotation of the closing element in relation to the base element when the connector means for administering medication to the aperture in the flange of the closing element is not present. Hereby unintended rotation of the closing element in relation to the base element to a position where the aperture is aligned with the entry lumen is prevented. Such alignment could lead to a contamination of the infusion set interior and the infusion site. Examples of suitable means could include a biasing element forming part of the closing element or a biasing element forming part of the base element which in an unloaded position blocks the rotation of the closing element in relation to the base element.

Preferably means for securing said base element in relation to the skin of a patient are provided in connection with base element. It is, however, possible that such means are provided as one or more separate element(s). The securing means is usually an adhesive layer.

The cannula can be either a rigid cannula or a soft cannula. The rigid cannula is usually a steel cannula although other possibilities exist. The soft cannula is usually a PTFE cannula. It is however possible to employ several other polymer material cannulas having similar characteristics for this purpose.

In case said cannula is a soft cannula, there is a need for a support of this during the insertion. In this connection said cavity extends to the top of said hub and self-sealing means covering said cavity towards said top of said hub are provided. An insertion needle is provided for removable insertion through an opening in said closing element, through said self-sealing means and through said cavity and said lumen of said soft cannula and extending beyond the length of said soft cannula.

The invention further relates to an infusion part for use in a subcutaneous infusion set as defined above, the infusion part comprising:
 a base element having a cavity and an entry lumen;
 a cannula mounted in and extending from said base element, said cannula having a lumen therethrough, said lumen communicating with the entry lumen through said cavity;
 a closing element mounted on said base element to be rotatable about an axis through said base element and having an aperture, where the aperture in one position of the closing element in relation to the base element is aligned with said entry lumen of said base element and in a further rotated position of the closing element in relation to the base element the closing element covers said entry lumen in said base element.

This part may be provided as a separate element for the infusion set reusing the connector.

The infusion part may further comprise the features as set forth above in cinnection with the infusion set.

DESCRIPTION OF THE PREFERRED EMBODIMENTS

Figure 1:
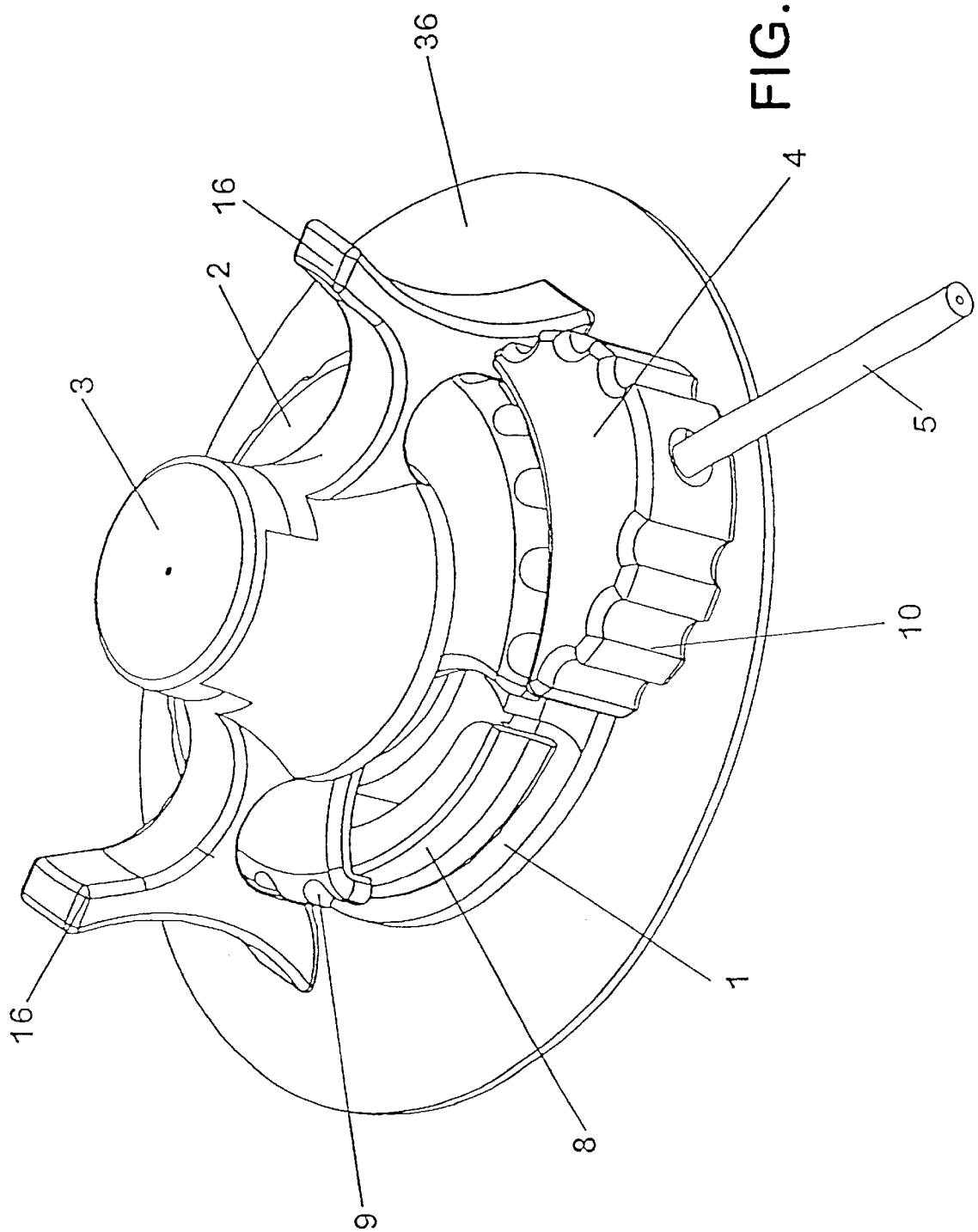
FIG. 1 is a perspective view of an infusion set comprising all the features of the invention.

A preferred embodiment of the subcutaneous infusion set according to the invention which is shown in FIG. 1 comprises the following elements: a base element 1, a closing element 2, a needle hub 3 with an insertion needle 14 (FIG. 5) and connector means 4 comprising a hose 5 for connecting the infusion set to further parts of the infusion set. The base element 1 is on the bottom side provided with an adhesive layer 36 which serves to secure the infusion set to the skin of the patient during use. This configuration corresponds to the situation before and immediately after the insertion of the needle 14 and the cannula 13 into the subcutaneous fat layer of a patient. After placement the insertion needle 14 is removed and can be discarded since the initial insertion is the only use of this. On both the closing element 2 and the connector 4 grooves 9 and 10 have been provided in order to improve the grip for the user hereby facilitating the rotation of the closing element.

Figure 2:
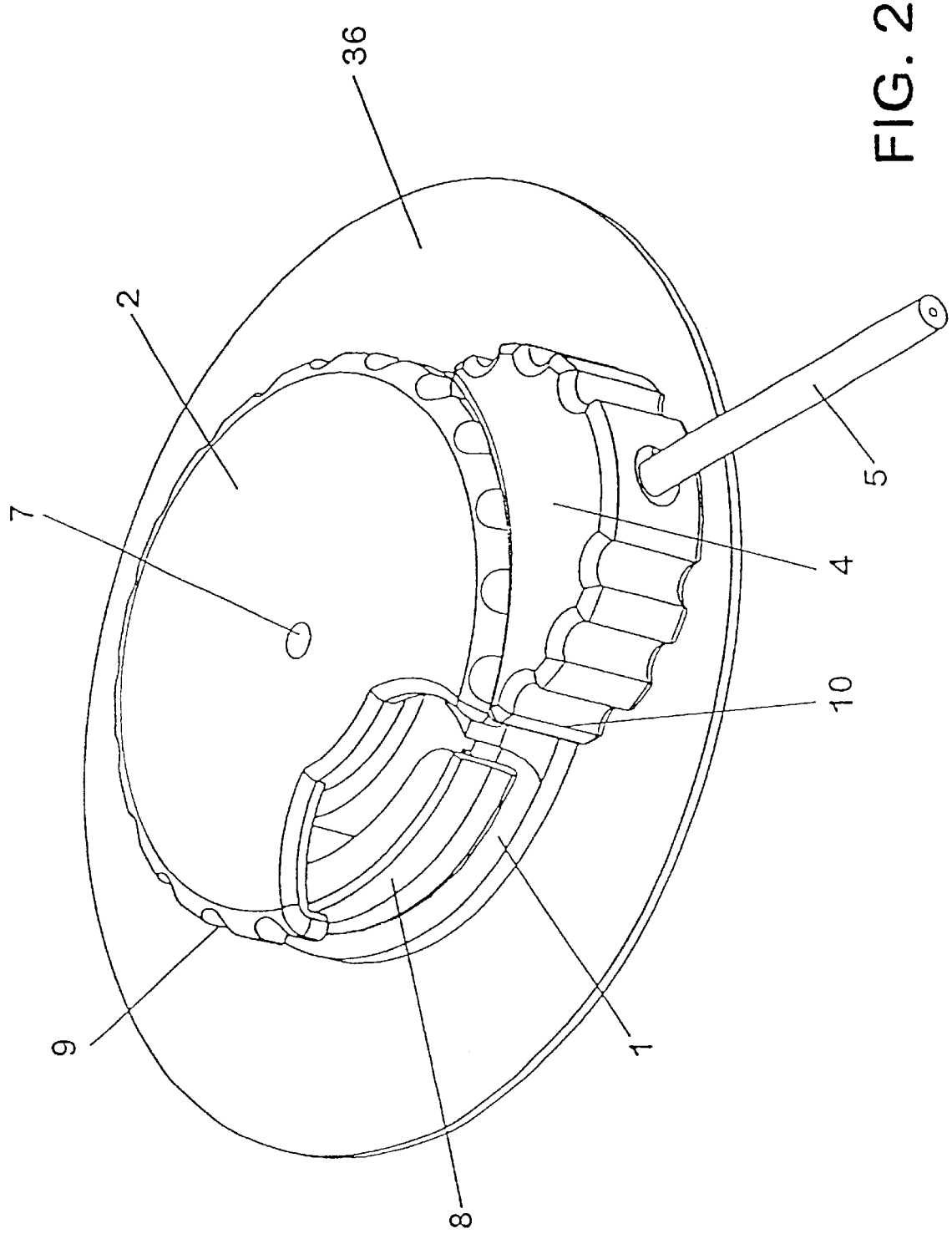
FIG. 2 is a perspective view of an infusion set corresponding to FIG. 1 where the insertion needle has been removed.

In FIG. 2 the insertion needle 14 has been removed from the infusion set. The infusion set can hereby remain on the patient for several days secured by the adhesive layer 36.

Figure 5:
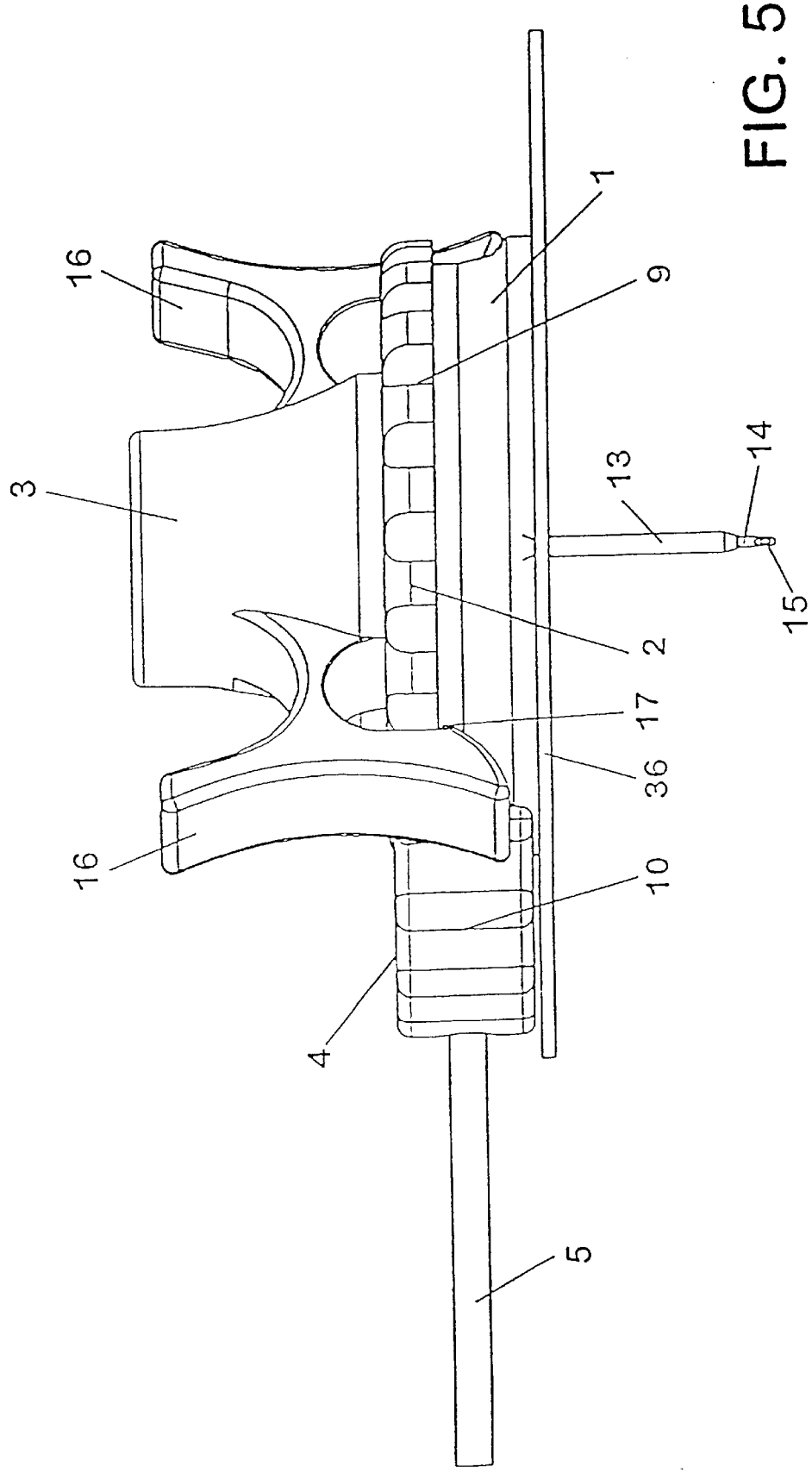
FIG. 5 is a side view of the device shown in FIG. 1.

From FIG. 5 it appears that the arms 16 of the needle hub are provided with projections 17 which interlock the needle hub 3 and the closing element 2. This feature serves to secure the needle 14 against axial displacement during the insertion process. After having completed the insertion process, the needle hub 3 and the needle 14 are removed by urging the arms 16 towards each other and at the same time withdrawing the needle hub 3. It appears that the needle, which is hollow, has an aperture 15 at its outer tip.

Figure 3:
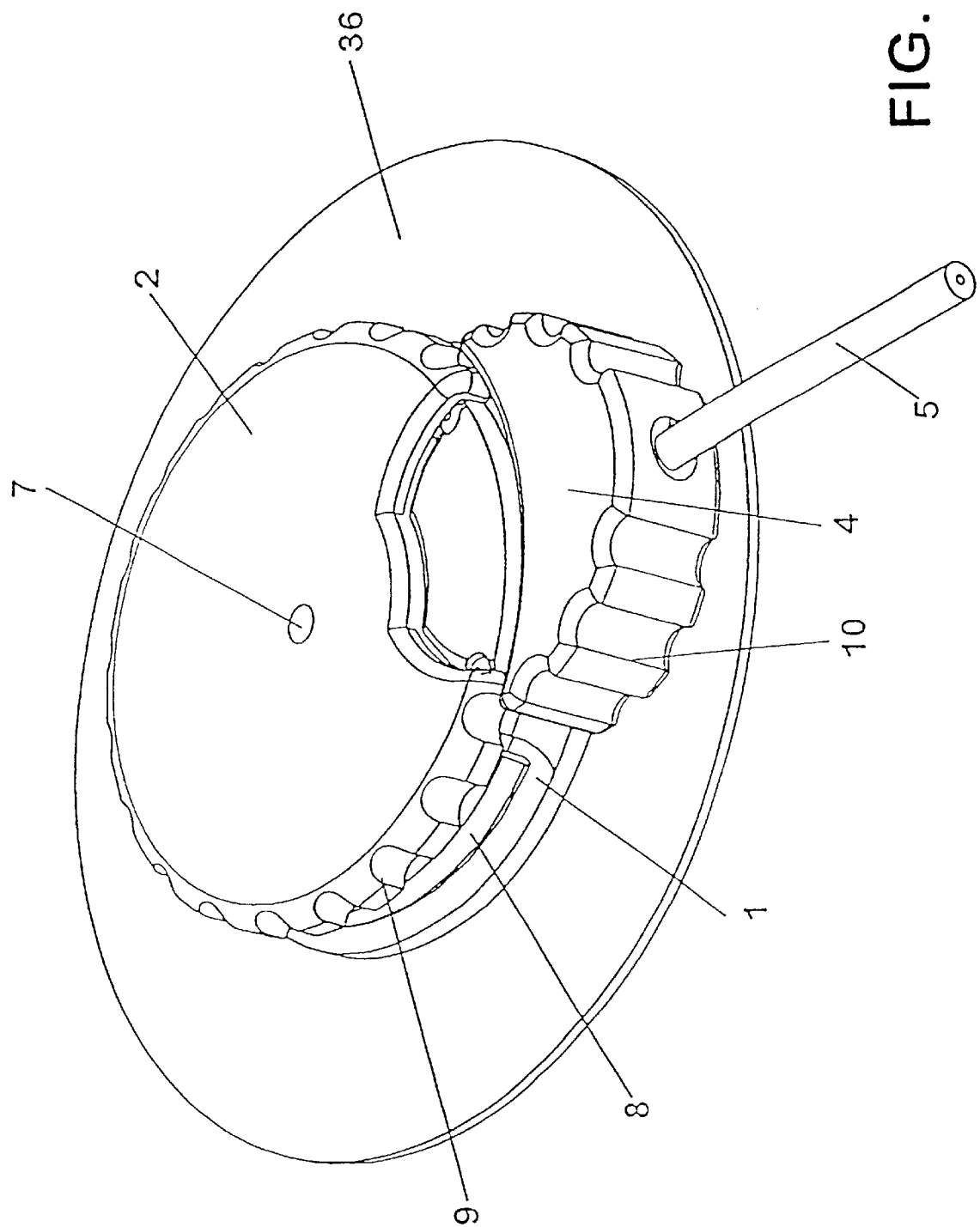
FIG. 3 is a perspective view of an infusion set corresponding to FIG. 2 where the closing element bias been rotated to a release position.
Figure 4:
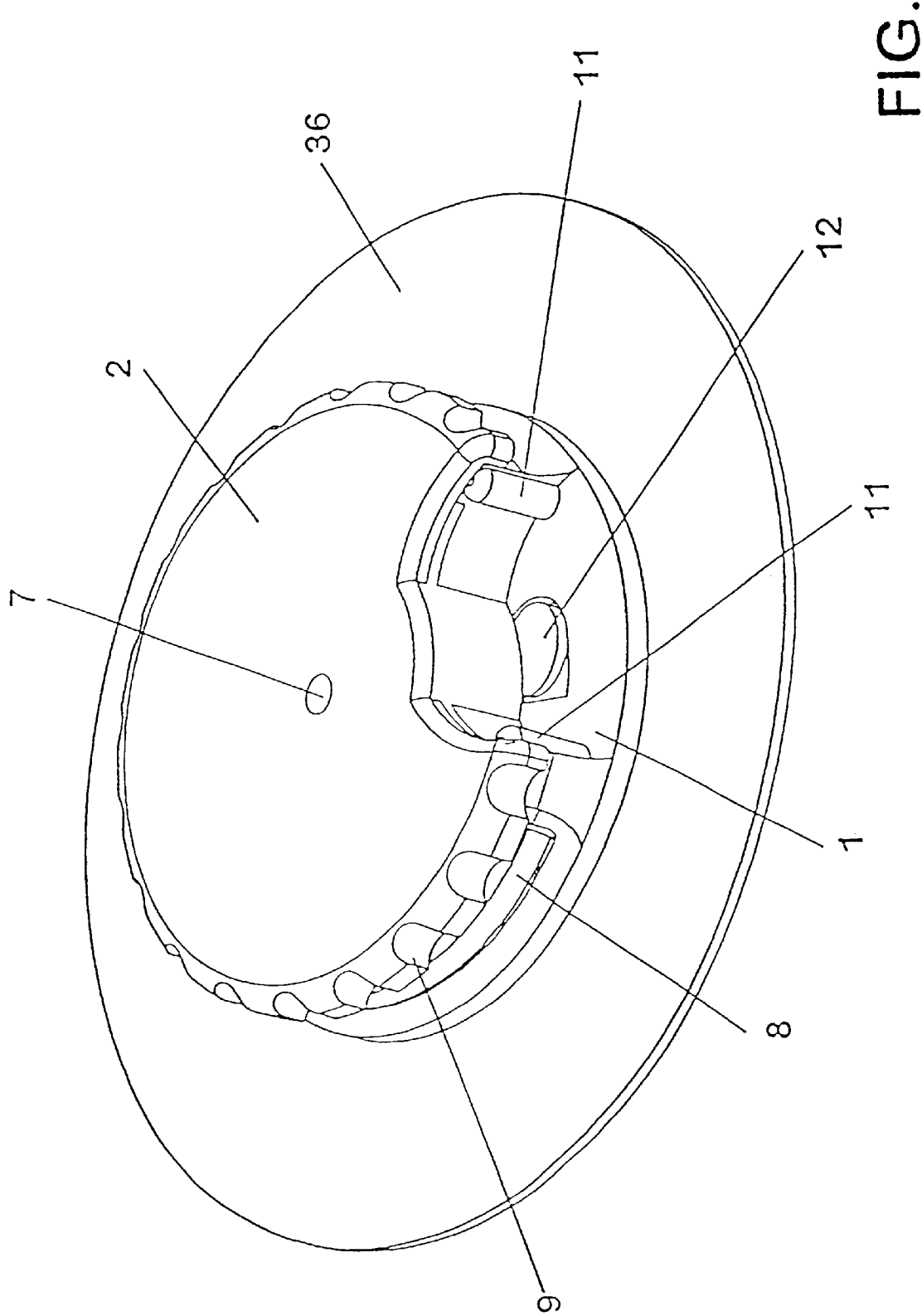
FIG. 4 is a perspective view of an infusion set corresponding to FIG. 3 where the connector means has been removed.

The closing element 2 is mounted to be rotatable in relation to the base element 1. The closing element 2 is rotatable about a central axis which in this embodiment extends co-axially with the longitudinally axis of the insertion needle 14 and the cannula 13. The rotation can take place between two extreme positions, namely a first position where the connector means 4 is secured in relation to the closing element 2 and the base element 1 as shown in FIG. 2, and a second position where the connector means 4 is releasable from the closing element 2 and the base element 1, as shown in FIG. 3. In FIG. 4 the base element 1 and the closing element 2 are shown where the connector means 4 has been removed. It appears that since projections 11 on the base element and corresponding grooves in the connector means have been provided, these projections 11 and grooves being parallel with the axis of rotation, the removal of the connector means 4 can only take place in an upward direction parallel with this axis. FIG. 4 further shows means for preventing unintended rotation of the closing element in relation to the base element. These means comprise a biasing element 12 which, in the unloaded state and upon an attempt to rotate the closing element, will abut the adjacent part of the base element 1 and thereby stop the rotation. Such rotation will lead to an opening to the infusion site which could cause a contamination.

From FIG. 5 it appears that the needle 14 mounted in the needle hub 3 protrudes beyond the length of the flexible cannula 13.

Figure 6:
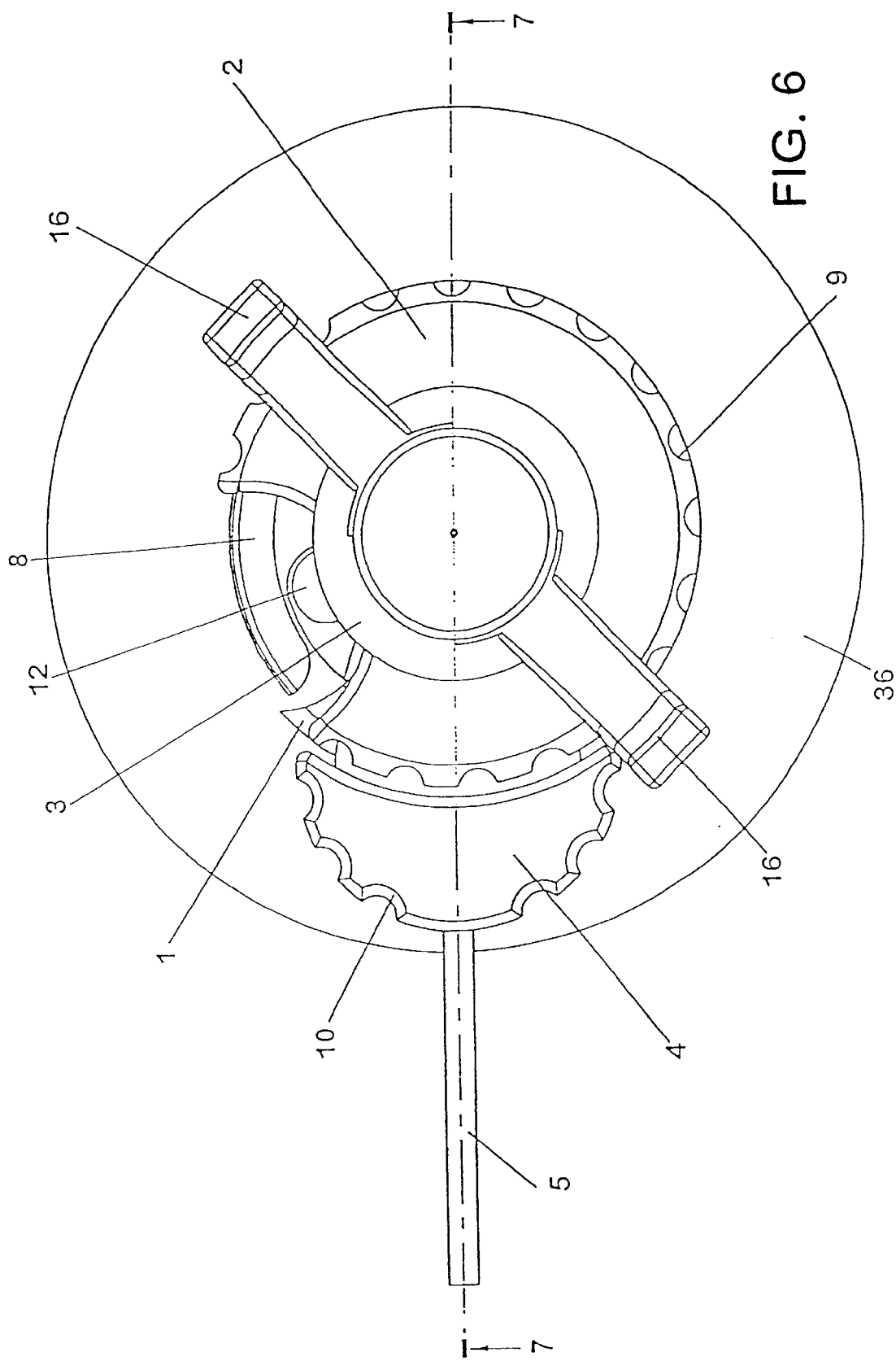
FIG. 6 is a top view of the device shown in FIG. 1.
Figure 7:
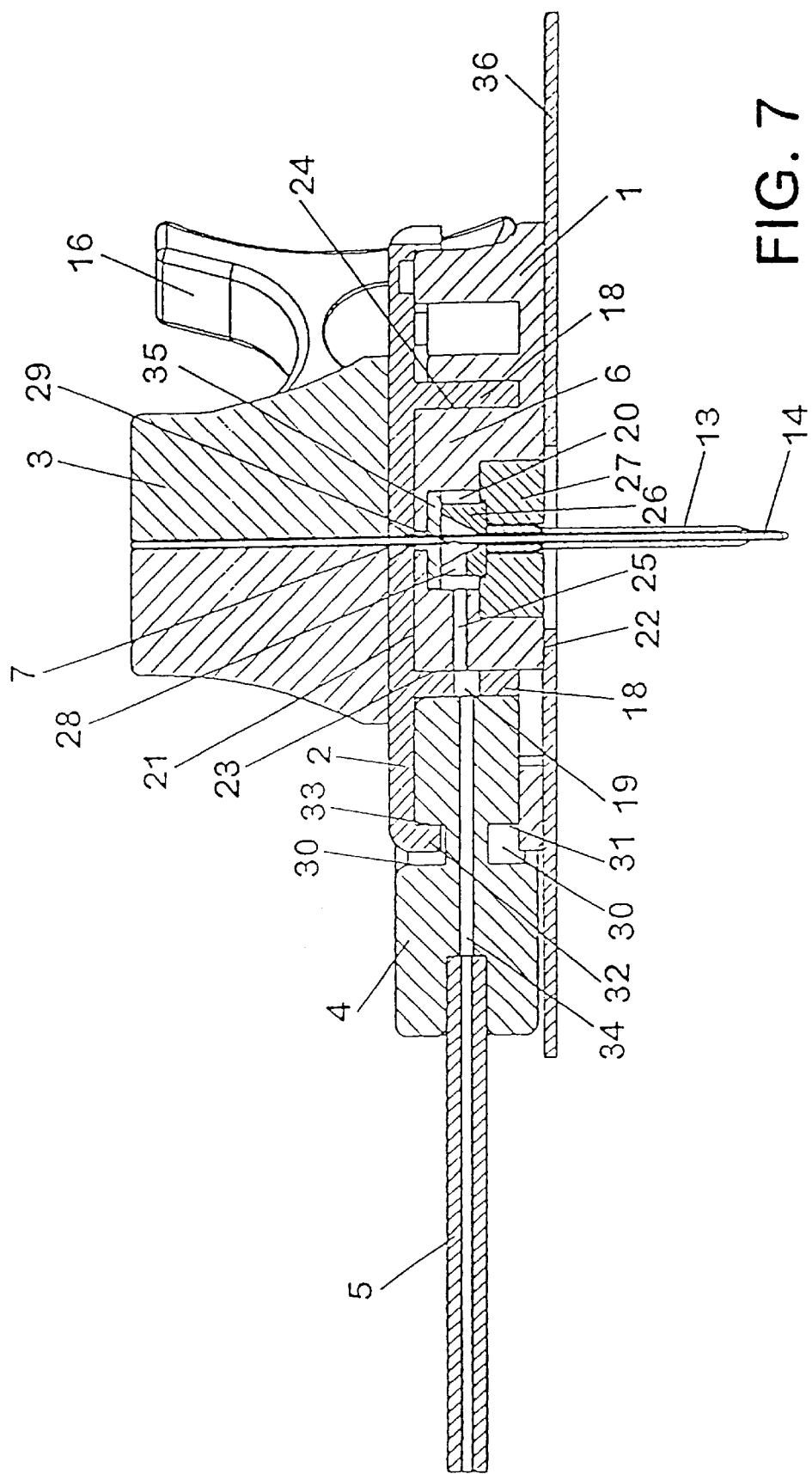
FIG. 7 is a sectional view taken along the line 7—7 in FIG. 6.

From FIG. 7 it further appears that the base element comprises a central hub 6 with a cavity 20 wherein means 26,27 for securing the soft cannula 13 are situated. Between the top 21 and the bottom 22 of this central hub 6 an outer surface 24 extends, and between the cavity 20 and the outer surface 24 an entry lumen 25 is provided. The closing element 2 comprises a flange 18 with an inner surface 23 which corresponds to the outer surface 24 of the hub 6. The two surfaces abut closely on each other. Between the inner surface and the outer surface of the flange 18 an aperture 19 is provided. In one of the previously mentioned extreme positions of rotation for the closing element 2 this aperture 19 is aligned with the entry lumen 25 in the hub 6, as shown in FIG. 6, whereby a fluid can be delivered from an external infusion system comprising a pump with a predetermined delivery rate through a hose 5 and a bore 34 in the connector means. In the other extreme position of rotation for the closing element 2, the flange 18 is covering the entry lumen 25 and thereby blocking the delivery of fluid. From FIG. 7 the path for the insertion needle 14 becomes apparent. The needle 14 is secured in the needle hub 3. The needle 14 is inserted through a hole 7 in the closing element and protrudes through a self-sealing septum 35 which separates a cavity 20 within the base element 1 from the surrounding environment, protrudes further through this cavity 20 and through the means 26,27 for securing the soft cannula 13 and through the lumen of the cannula 13 itself to a point beyond the outer tip of the soft cannula. The needle 14 hereby prepares the way for the soft cannula 13 during the insertion process. The septum is made from a usual flexible polymer material. It is apparent from the foregoing description that the septum is only penetrated once by the insertion needle.

The means as shown for securing the cannula are provided in case the cannula is of a type which cannot be secured directly to the base element by e.g. gluing or welding. This is the case if the cannula is made from PTFE. The means comprise a first element 26 inserted in the cannula and a second element 27 fitted around the cannula in the area where the first element 26 has been inserted, hereby providing a firm grip around the cannula. The element 27 can then be secured in relation to the base element. In the shown embodiment the element 26 abuts the septum 35 hereby supporting this.

Figure 8:
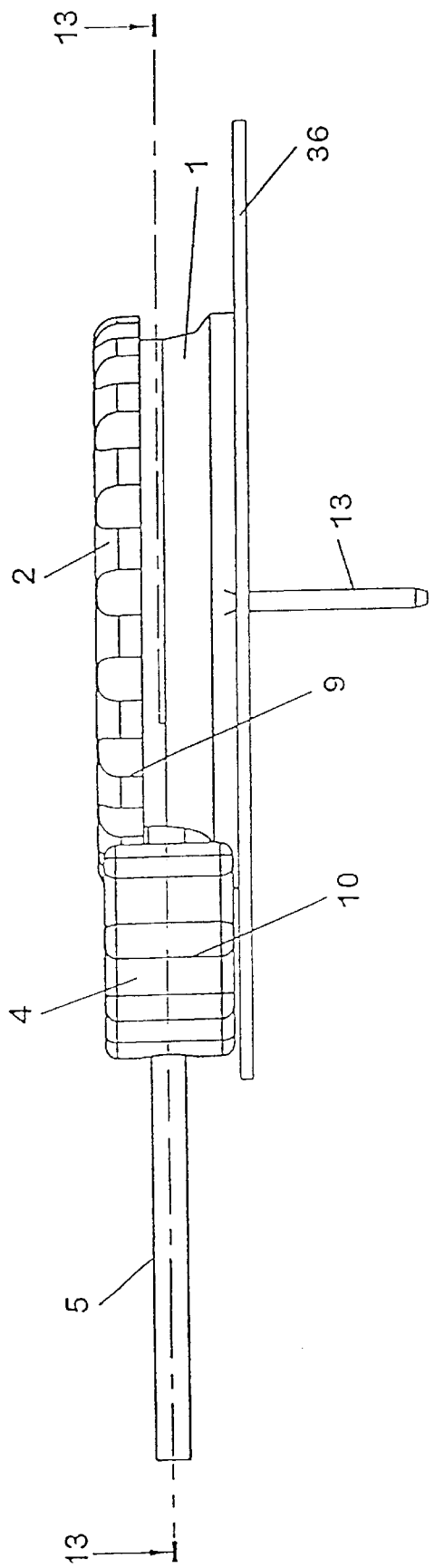
FIG. 8 is a side view of the device shown in FIG. 2.

From FIG. 8 a side view of the infusion set in the normal open position for the aperture in the flange of the closing element is shown.

Figure 9:
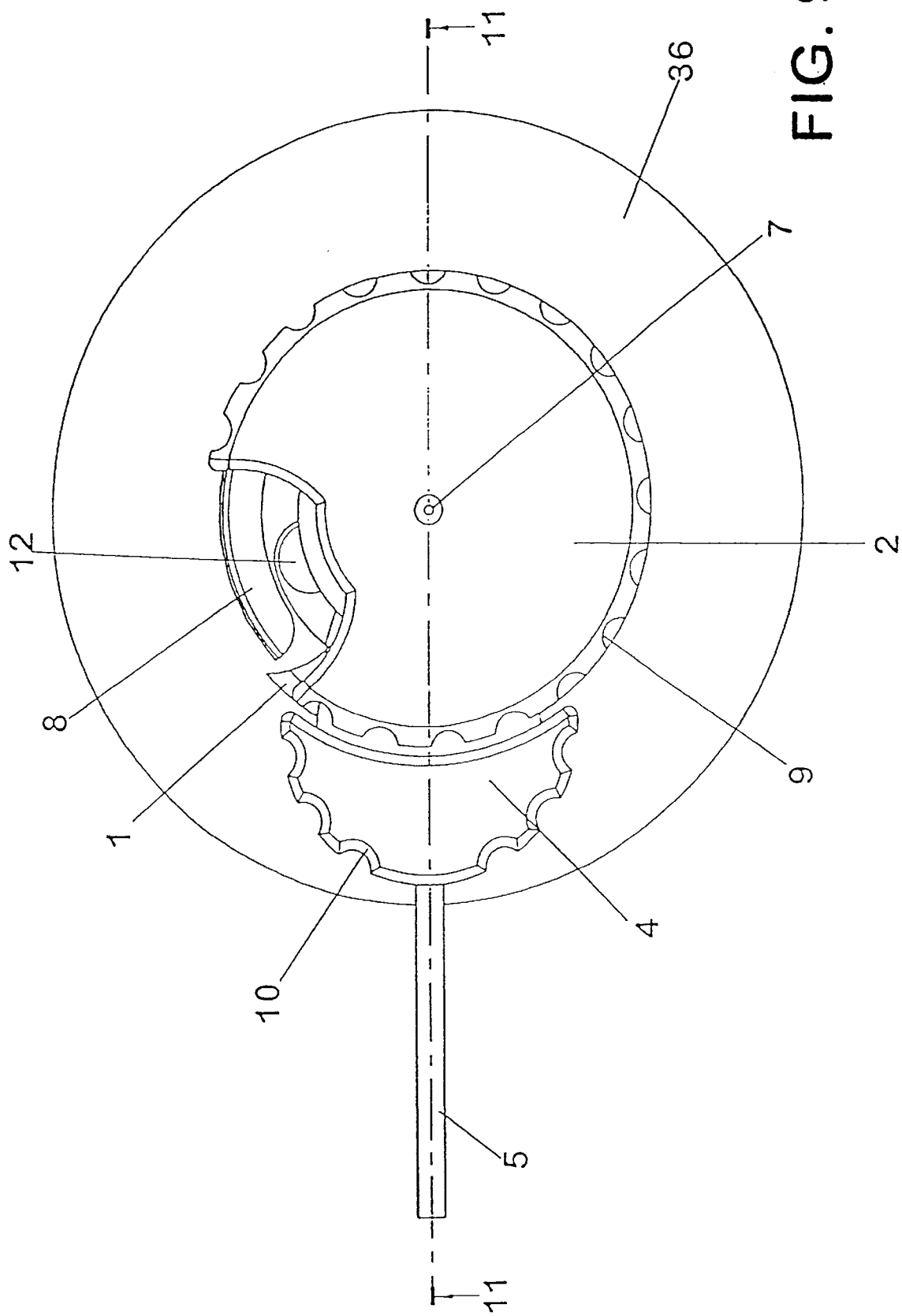
FIG. 9 is a top view of the device corresponding to FIG. 2.
Figure 10:
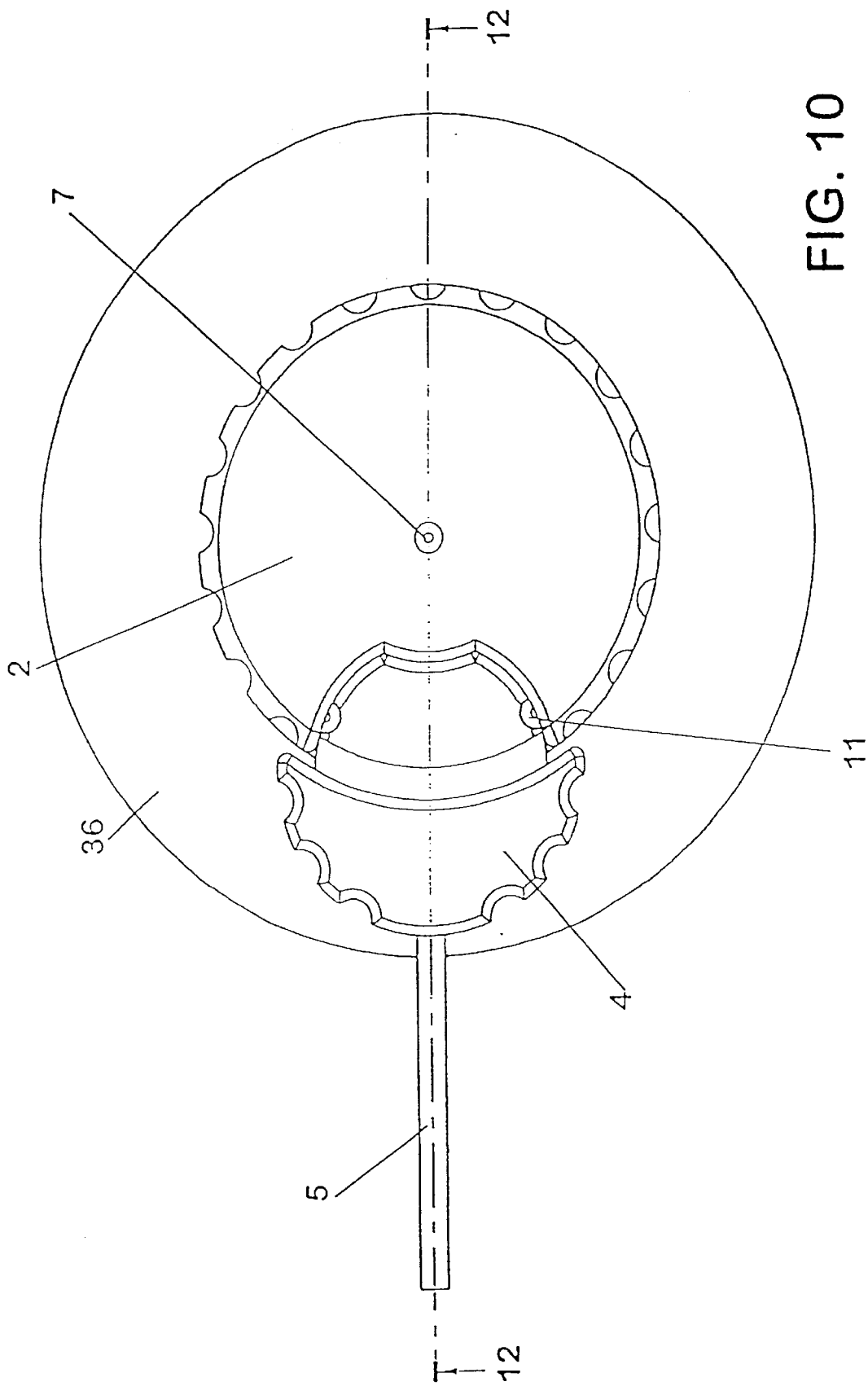
FIG. 10 is a top view corresponding to FIG. 3 where the closing element has been rotated to a release position.

FIG. 9 and FIG. 10 are top views of the infusion set in an open position and a closed position, respectively, for the aperture in the flange of the closing element in relation to the entry lumen in the hub.

Figure 11:
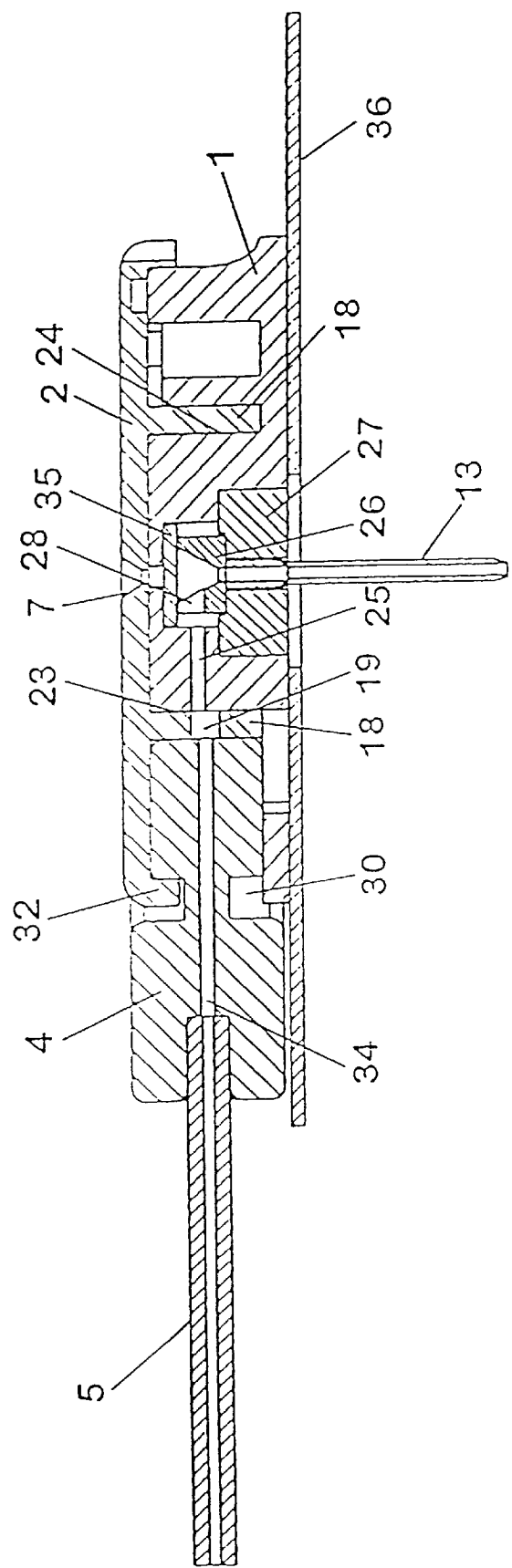
FIG. 11 is a sectional view taken along the line 11—11 in FIG. 9.
Figure 12:
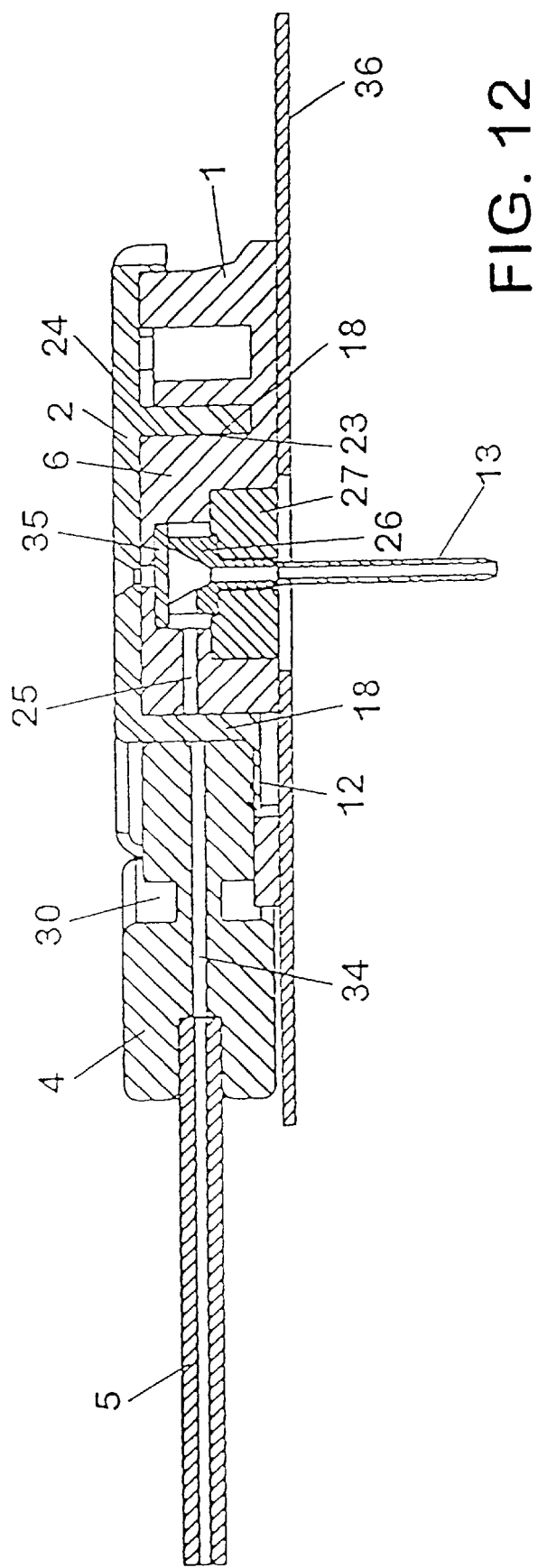
FIG. 12 is a sectional view taken along the line 12—12 in FIG. 10.

FIG. 11 and FIG. 12 are vertical sectional views of the infusion set in an open position and a closed position, respectively, for the aperture 19 in the flange 18 of the closing element 2 in relation to the entry lumen 25 in the hub 6. In the open position an inwardly facing surface 33 of an outer flange 32 extending downwards from the outer rim of the closing element urges against an outwardly facing surface 31 of the connector means 4 hereby urging the connector means towards the inner flange 18 comprising the aperture 19 which forms part of the flow path. In the closed position the connector means 4 is not influenced by the flange 32 and can therefore be removed from the base element 1 and the closing element 2. Due to this urging effect upon rotation of the closing element 2 towards the open position an air- and fluid-tight sealing between the connector means 4 and the inner flange 18 can be obtained. Between the inner flange, 18 and the hub 6 the sealing effect is provided due to a close fitting of the outer surface 24 of the hub 6 and the inner surface 23 of the flange 18. It is however possible to provide sealing means 244 between the connector means 4 and the inner flange 18 and/or the inner flange 18 and the central hub 6. Such sealing means could comprise O-rings or the like suitable for use in connection with the medical purpose of the infusion set. It appears further that the connector 4 is symmetrical about a horizontal plane which eliminates the risk of incorrect positioning of the connector 4 in relation to the base element 1.

Figure 13:
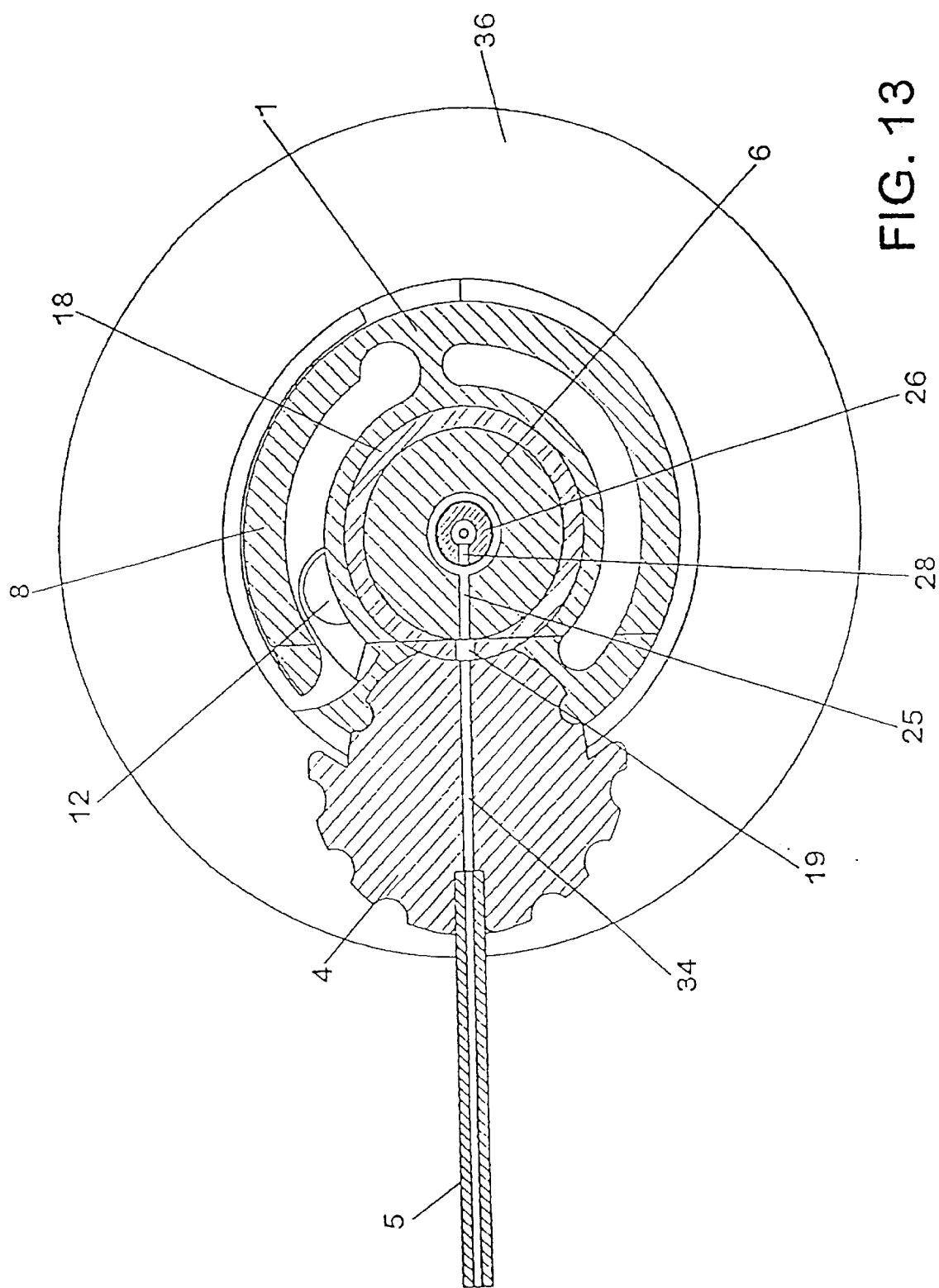
FIG. 13 is a sectional view taken along the line 13—13 in FIG. 8.
Figure 14:
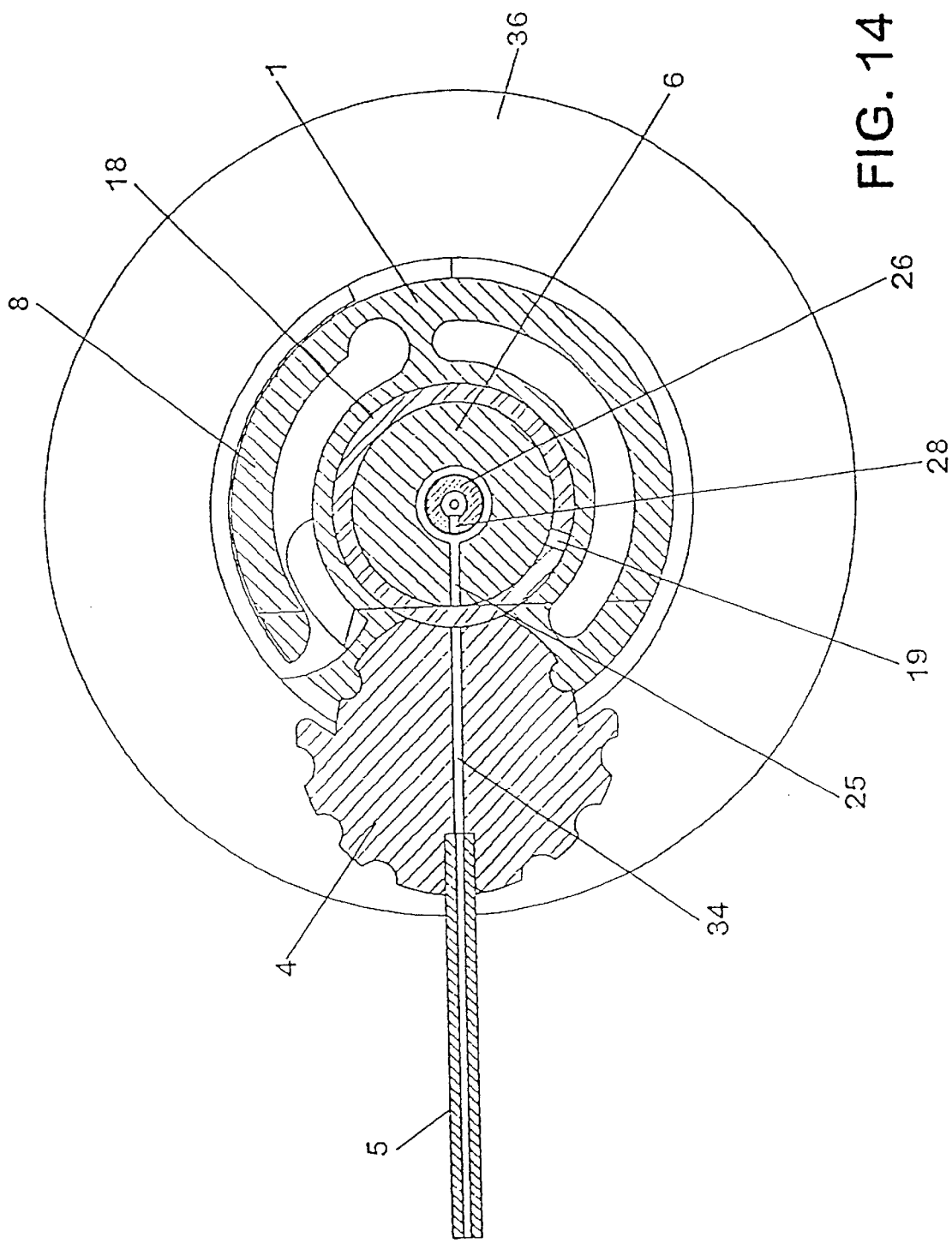
FIG. 14 is a sectional view corresponding to FIG. 11 where the closing element has been rotated to a release position.

The position of the aperture 19 in the inner flange 18 of the closing element 2 in the open position and the closed position becomes more apparent from the horizontal sectional views shown in FIG. 13 and FIG. 14, respectively. In FIG. 13 the flow path is shown through the hose 5, the connector 4, the aperture 19 in the flange 18, the entry lumen 25 in the hub 6 and a slit 28 in the means 26 for securing the soft cannula 13 and the cannula itself which leads the fluid to the subcutaneous infusion site. In FIG. 14 the closing element 2 has been rotated whereby the flange 18 covers the entry lumen 25 and thereby shuts off the flow path between the connector means 4 and the entry lumen 25. The entry lumen 25 is in this position for the closing element 2 sealed to be fluid-tight with respect to the environment. It appears that the connector 4 around the outlet has a surface corresponding to the outer surface of the inner flange 18. This is necessary in order to provide the above mentioned fluid-tight sealing between the connector 4 and the flange 18.

Figure 15:
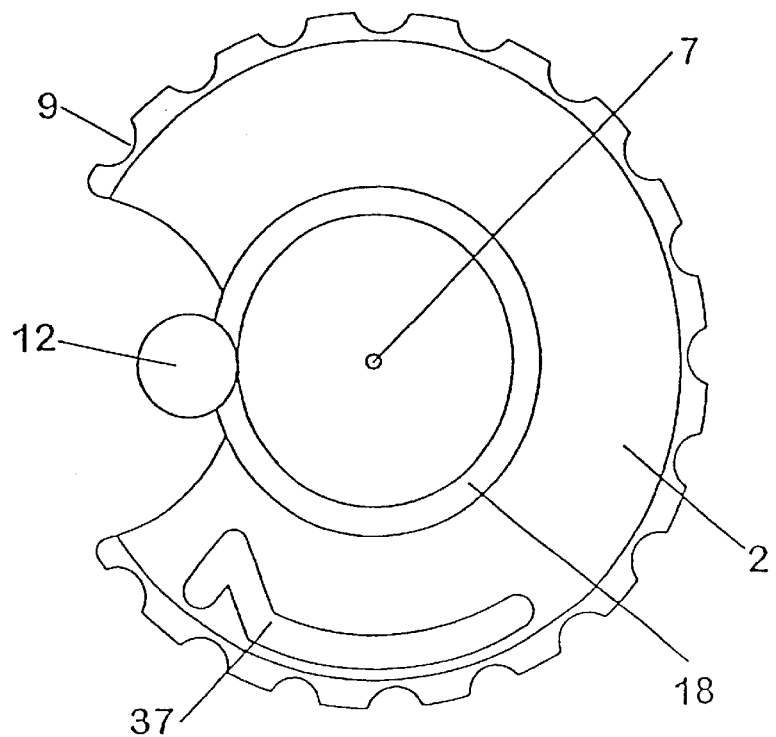
FIG. 15 is a bottom view of the closing element.
Figure 16:
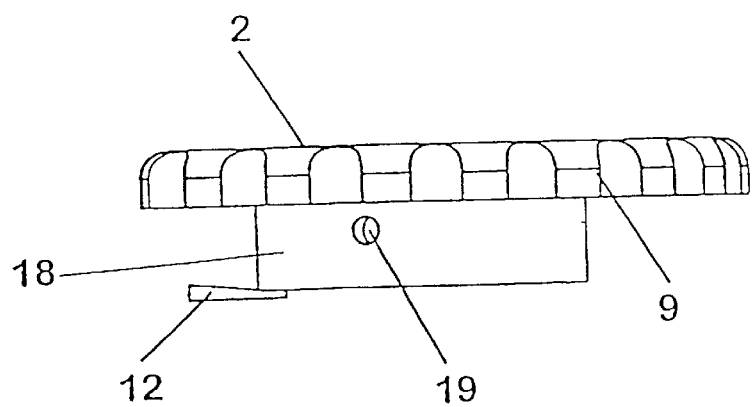
FIG. 16 is a side view of the closing element.
Figure 17:
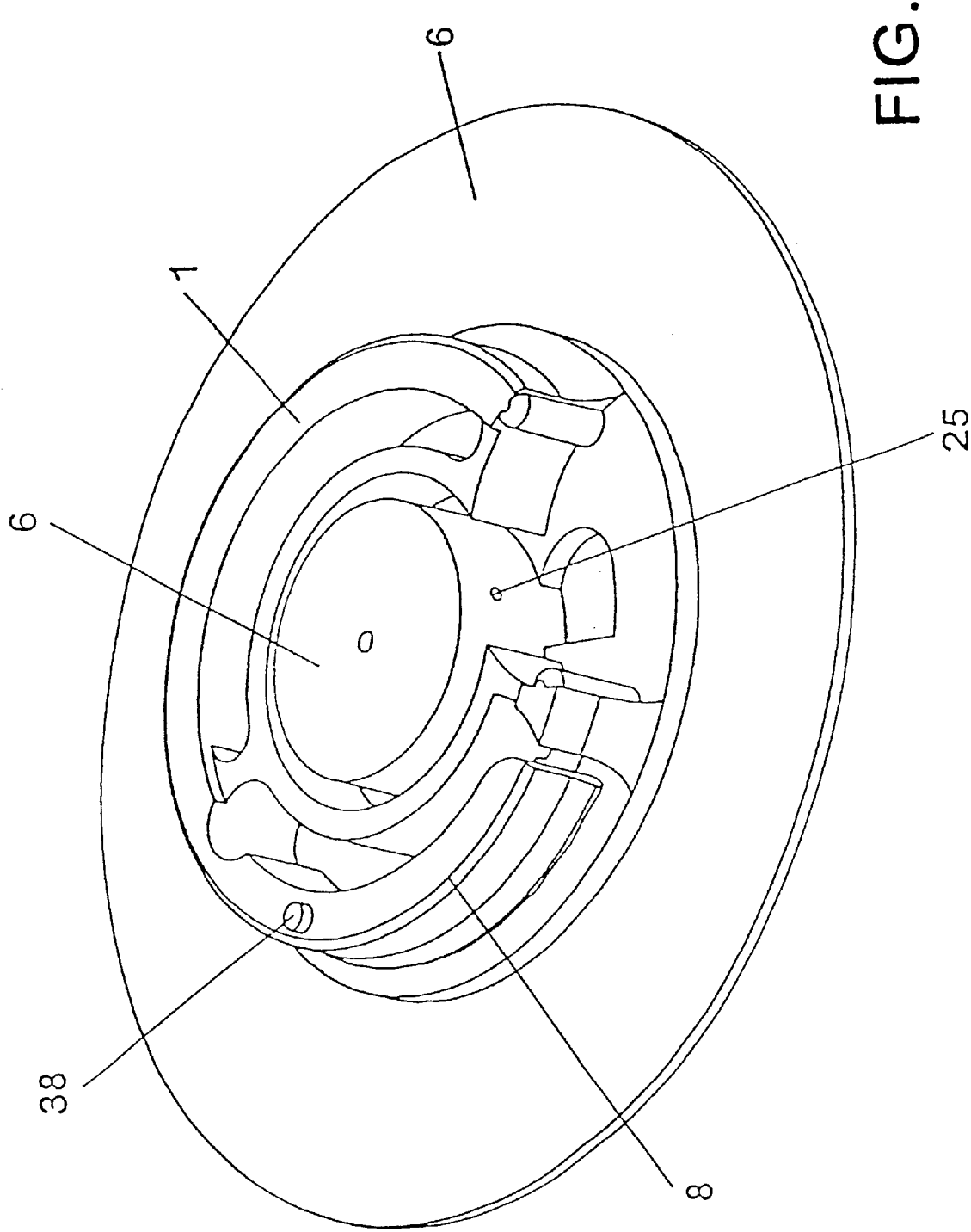
FIG. 17 is a perspective view of the base element.

From FIG. 15 it appears that a groove 37 is provided in the bottom side of the closing element 2 facing the base element 1. On the top of a flexible locking arm 8 forming part of the base element 1, a knob 38 (FIG. 17) is provided which co-operates with the groove 37 in the closing element 2. The groove is formed to lock the knob 38 in the so-called open position where the aperture 19 in the flange 18 is aligned with the entry lumen 25. Hereby an unintended rotation of the closing element 2 is widely precluded as a rotation will necessitate a preceding release of the knob 38 from the groove 37. The release is caused by pushing of the flexible locking arm 8 towards the central part 6 of the base element 1. The rotation must be effected simultaneously with the pushing of the locking arm 8. This combined pushing and rotation impedes the unintended rotation and thereby improves the safety of the device in use.

The biasing element 12 has previously been described as regards prevention of unintended rotation of the closing element during absence of the connector 4. In the presence of the connector 4 and in the open position the biasing means 12 rests in an unloaded position as shown in FIG. 6. Hereby undesired fatigue which could have been caused by constant load is prevented which ensures the functionality of this feature after a long-term storing period.

Figure 18:
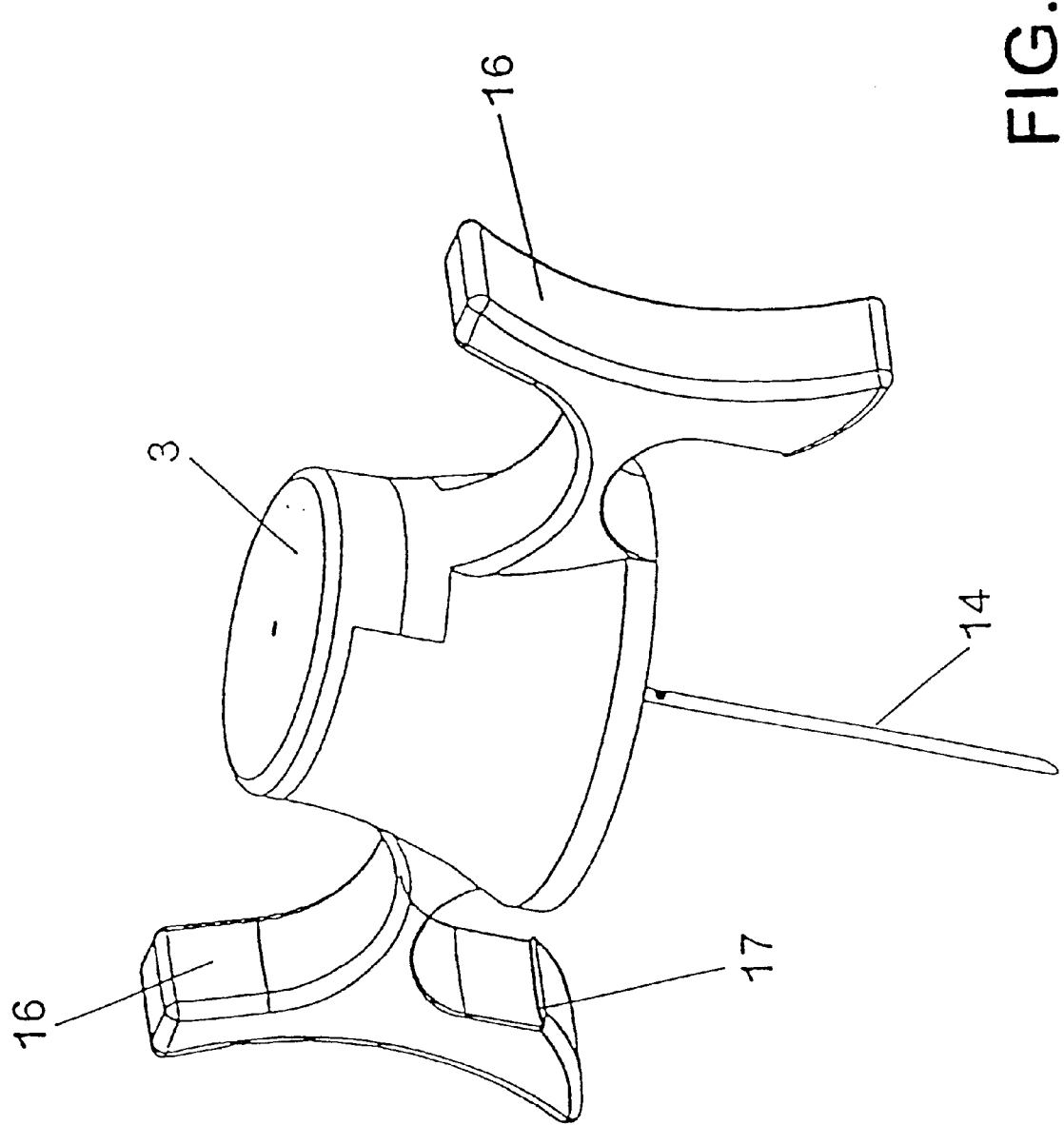
FIG. 18 is a perspective view of an insertion needle.

The needle hub 3 and the insertion needle 14 appears from FIG. 18.

Figure 19:
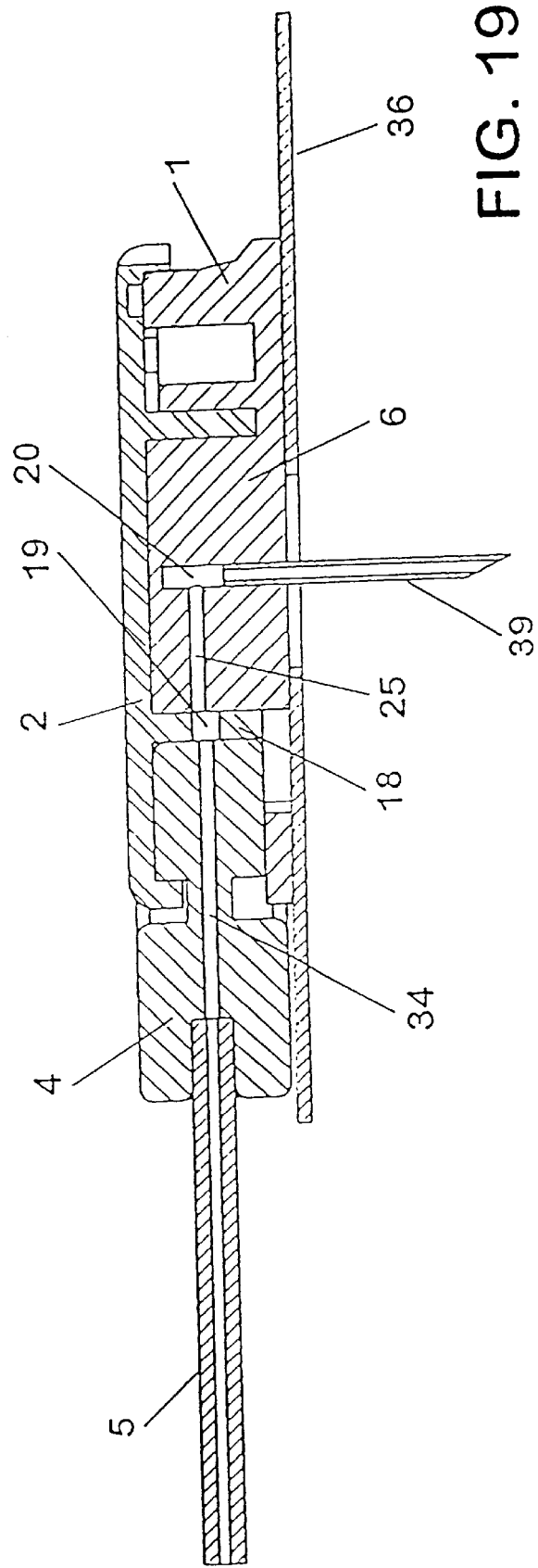
FIG. 19 is a sectional view of an infusion set provided with a rigid cannula.

In FIG. 19 an embodiment with a rigid cannula 39, preferably a steel cannula, is shown in section. It appears that similar elements as shown in connection with the embodiment of FIGS. 1–18 for the opening and closing of the entry lumen are present in this embodiment. The aperture 7 in the closing element 2, the upper opening in the hub 1 and the septum 35 have been omitted since there is no need for an insertion needle due to the rigidity of the cannula.

Figure 20:
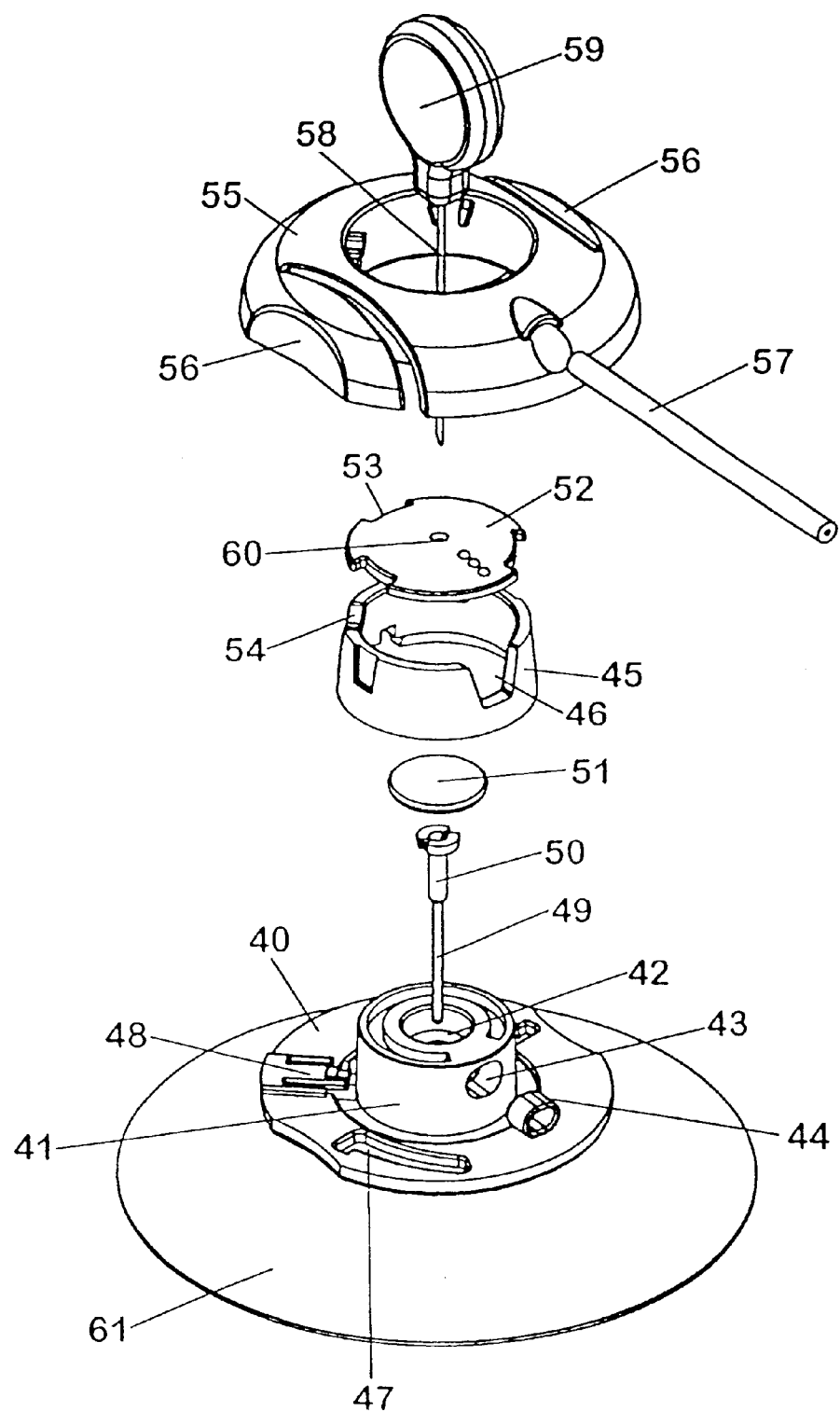
FIG. 20 is an exploded view of a second preferred embodiment of the infusion set.

A second preferred embodiment of the subcutaneous infusion set according to the invention is shown in FIG. 20 in an exploded view. The infusion set comprises the following elements: a base element 40, a closing element 45, a needle hub 59 with an insertion needle 58 and connector means 55 comprising a hose 57 for connecting the infusion set to further parts of the infusion set such as a pump. The base element 40 is on the bottom side provided with an adhesive layer which serves to secure the infusion set to the skin of the patient during use. The base part comprises a hub 41 where a cavity 42 is provided. Between the side of the hub and the cavity 42 an aperture or bore 43 is provided. A sealing element in the form of an O-ring is provided in the aperture. In the lower end of the cavity a bore is provided for the placement of a hollow cannula 49 mounted in a likewise hollow bushing 50. A self-sealing membrane 51 is provided for closing the cavity. The closing element 45 is mounted over the hub 41 in such a manner that in one position an opening or cut-out 46 allows flow into the aperture 43 and in a further rotated position closes off the aperture sealing due to the presents of the sealing means 44. A lid part 52 is provided for securing the closing element 45 and the connector 55 against axial movement. A hole 60 in the lid part is provided for the insertion needle 58, 59. The connector 55 comprises a protruding part adapted to abut on the hub 41 or the sealing means in the hub where this part comprise a bore for the transport of the medication which is supplied through the hose 57. As a sealed contact is achieved between the connector and the base part the medication can be led to the cavity and from the cavity through the hollow cannula to the subcutaneous fat layer of the patient. The connector further comprises releasable locking means for connection in relation with the base part. The locking means are releasable through the gripping means situated at respective sides of the connector. The locking means comprises protruding taps on the connector (FIGS. 32, 33) adapted to cooperate with an angled path 47 in the base part.

Figure 21:
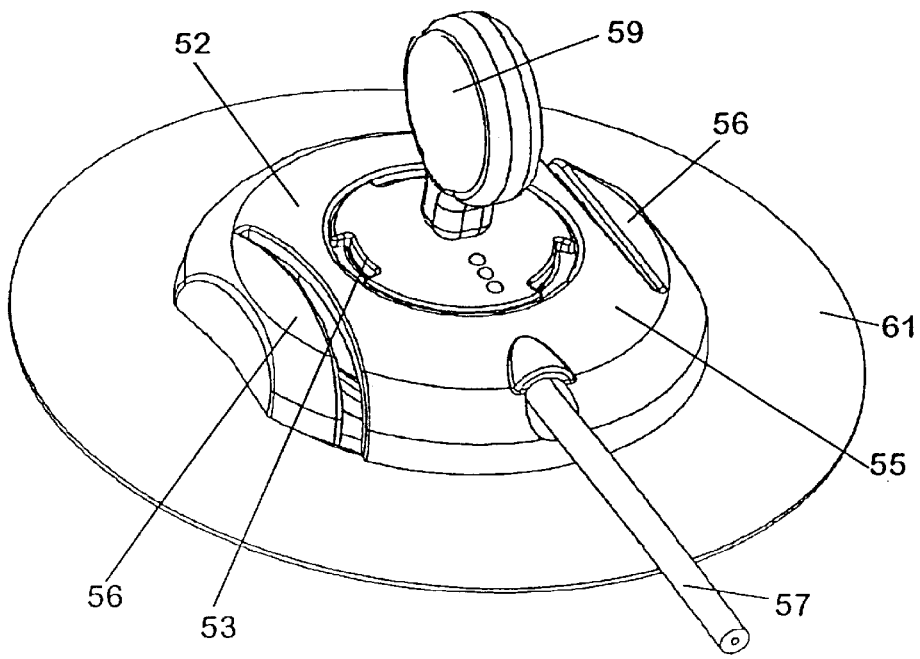
FIG. 21 is a perspective view of the infusion set of FIG. 20 in an assembled state comprising all the features of the invention.

The infusion set is shown in an assembled state in FIG. 21. The infusion set is ready for insertion as the insertion needle is in the insertion position. The bore in the connector is aligned with the aperture of the hub, which is indicated by the three centrally directed knobs on the lid part being aligned with the hose and the bore in the connector.

Figure 22:
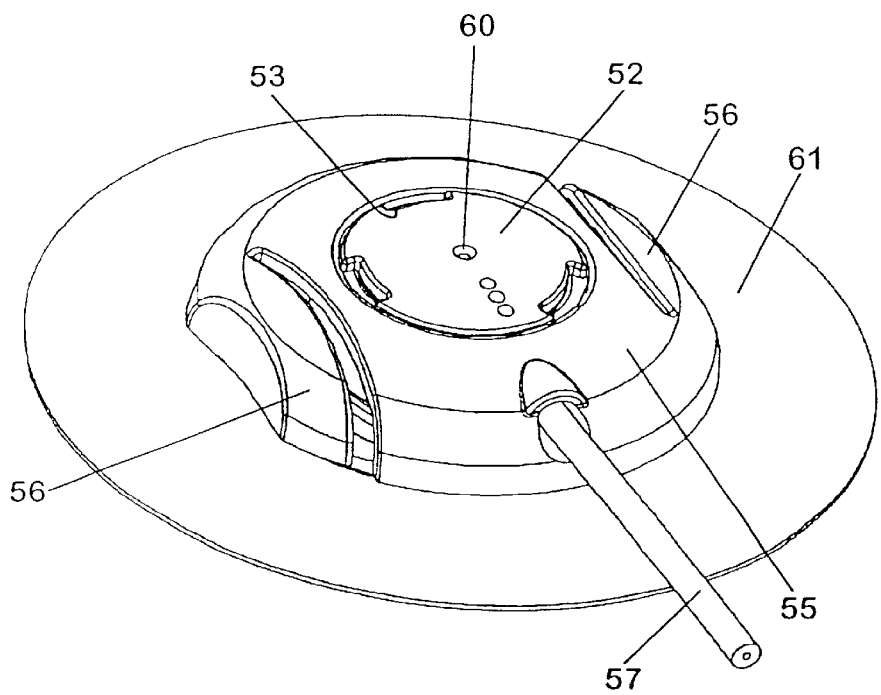
FIG. 22 is a perspective view of an infusion set corresponding to FIG. 21 where the insertion needle has been removed.

From FIG. 22 the infusion set appears in the configuration where the insertion needle 58,59 has been removed. The infusion set can hereby remain on the patient for several days secured by the adhesive layer 61.

Figure 23:
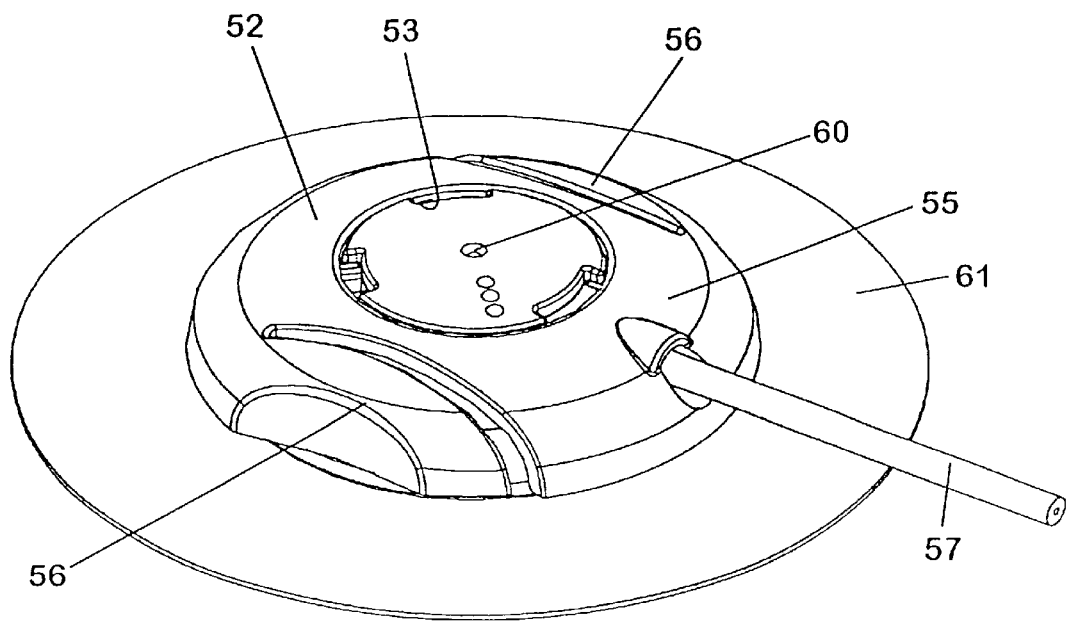
FIG. 23 is a perspective view of an infusion set corresponding to FIG. 22 where the closing element has been rotated to a release position.

From FIG. 23 it appears that the connector 55 has been rotated as the knobs are no longer aligned with the hose. In this position the cut-outs 53 in the lid part 52 are axially aligned with complementary protruding parts on the connector and the connector may be removed by axial displacement.

Figure 24:
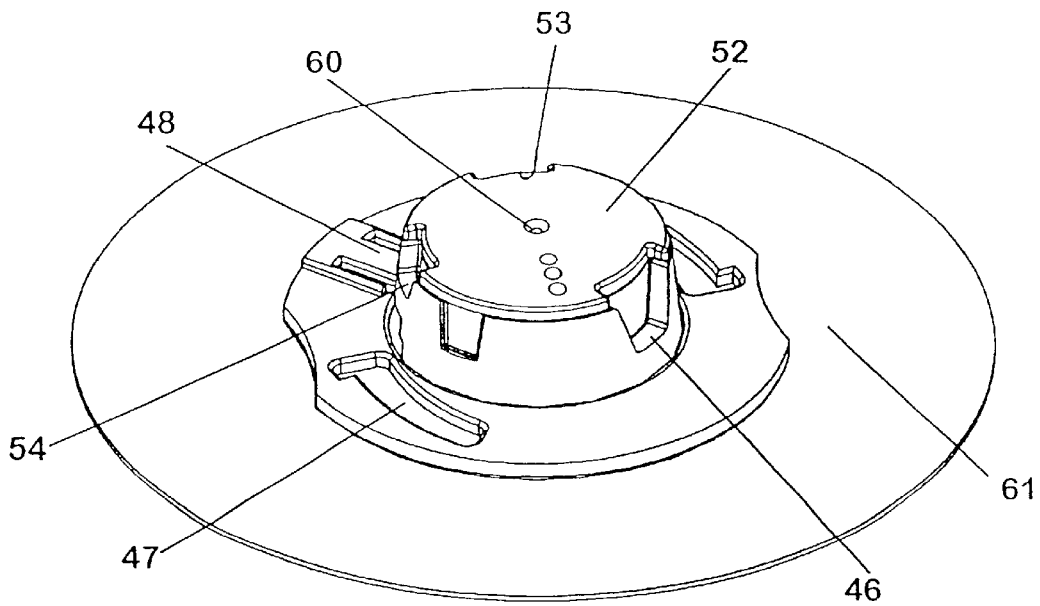
FIG. 24 is a perspective view of an infusion set corresponding to FIG. 23 where the connector means has been removed.

From FIG. 24 the infusion set appears in a state where the connector 55 has been removed. It appears that the aperture 43 is closed by the closing element 45 as the opening 46 is rotated away from the aperture and the sealing means sealingly abuts on the inwardly facing side of the closing element.

Figure 25:
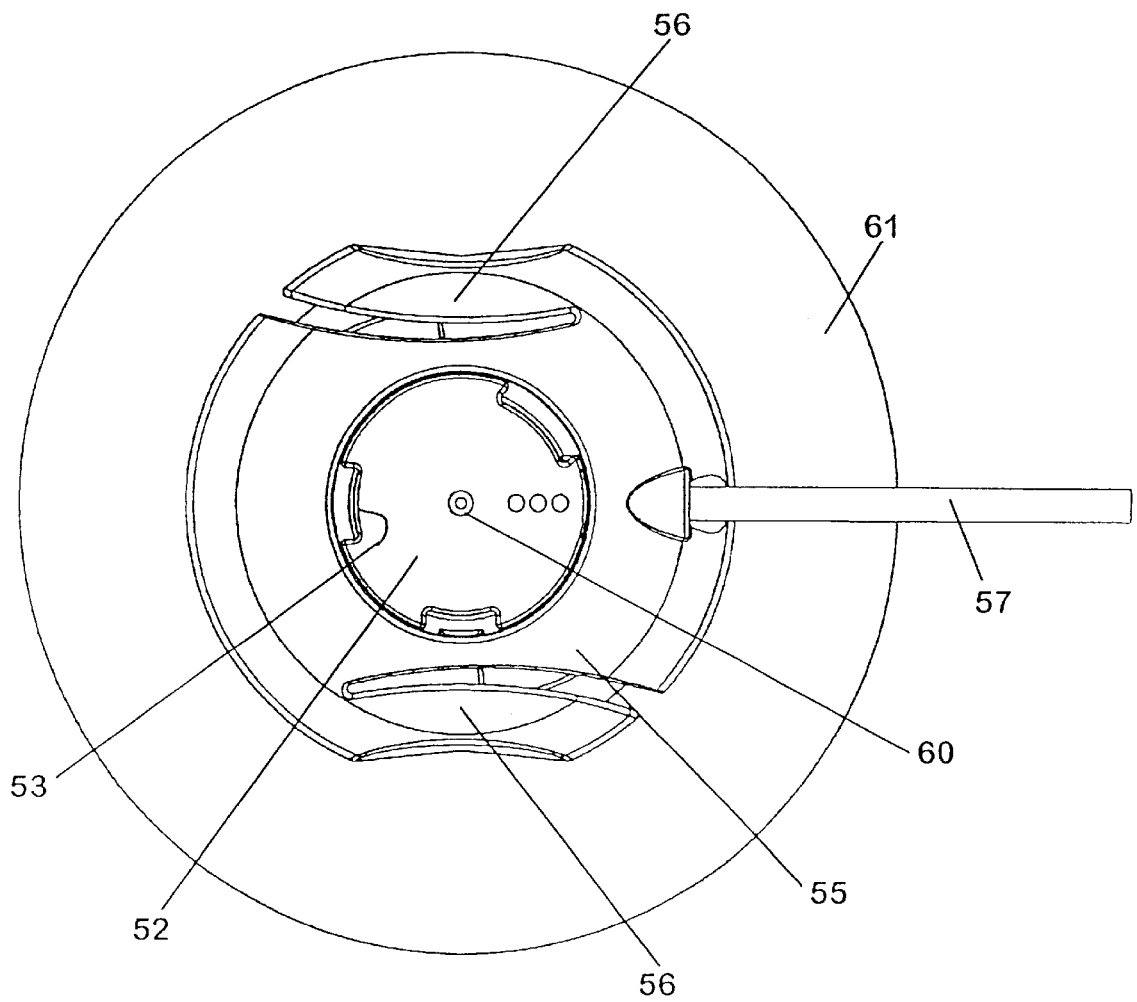
FIG. 25 is a top view of the device shown in FIG. 22.

From FIG. 25 the infusion set appears seen from above. It appears that the infusion set has an essentially circular base.

Figure 26:
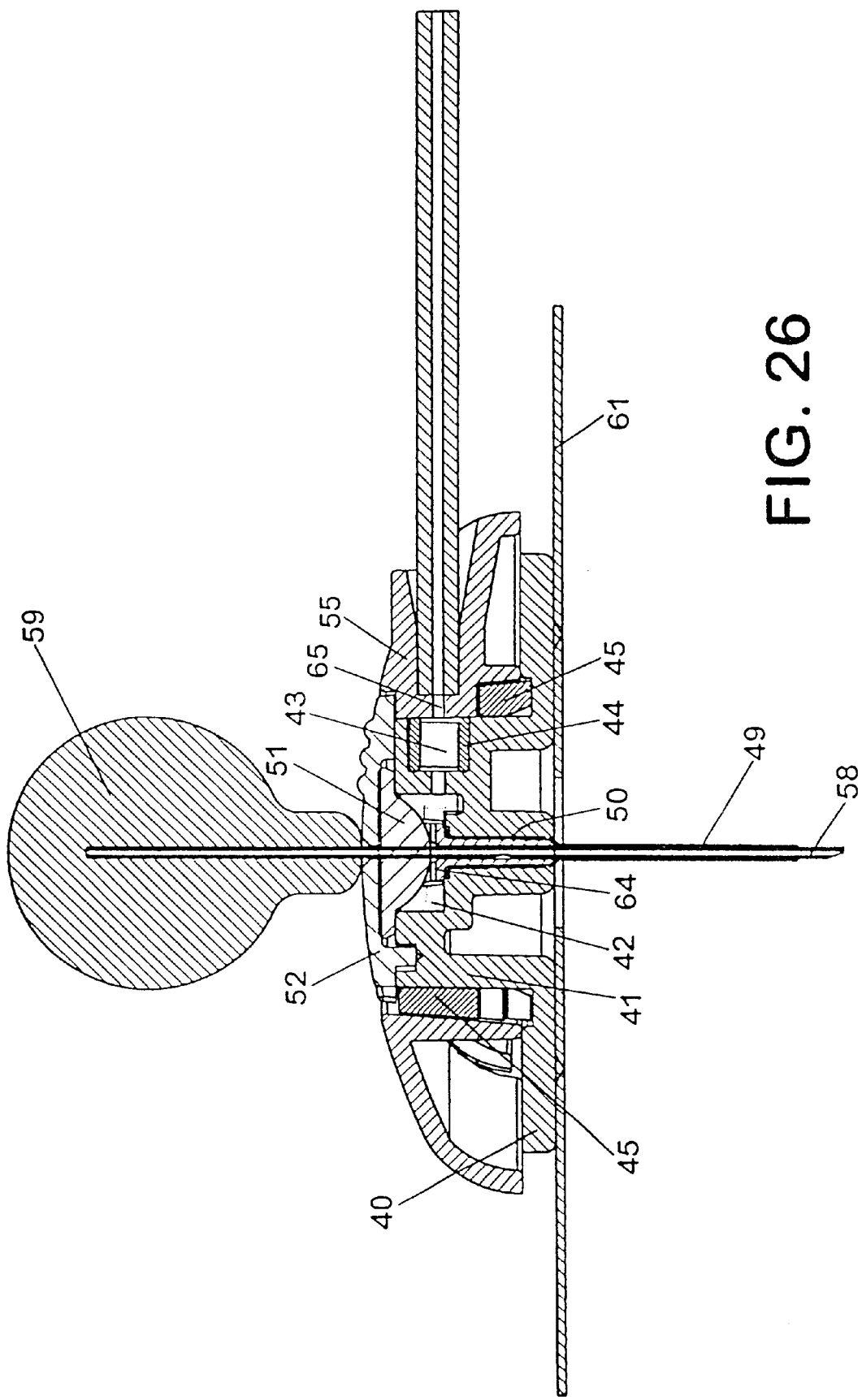
FIG. 26 is a sectional view taken along the line 26—26 in FIG. 21.

From FIG. 26 it further appears that the base element 40 comprises a central hub 41 with a cavity 42 wherein means 50 for securing the soft cannula,49 are situated. Between the top and the bottom of this hub 40, an outer surface extends and between the cavity 42 and the outer surface an entry lumen 43 is provided. The closing element 45 comprises a ring-shaped element with an inner surface which corresponds to the outer surface of the hub 40. The two surfaces abut closely on each other but allow rotation of the closing element 45. Between the inner surface and the outer surface of the closing element, an opening 46 in the form of a cut-out is provided. In one of the previously mentioned extreme positions of rotation for the closing element 45, this aperture 46 is aligned with the entry lumen 25 in the hub 41, as shown in FIG. 22, whereby a fluid can be delivered from an external infusion system comprising a pump with a predetermined delivery rate through a hose 57 and a bore 65 in the connector means. In the other extreme position of rotation for the closing element 45 is covering the entry lumen 43 and thereby blocking the delivery of fluid. From FIG. 26 the path for the insertion needle 58 becomes apparent. The needle 58 is secured in the needle hub 59. The needle 58 is inserted through a hole 60 in the lid element and protrudes through a self-sealing septum 51, which separates a cavity 42 within the base element 40 from the surrounding environment, protrudes further through this cavity 42 and through the means 50 for securing the soft cannula 49 and through the lumen of the cannula 49 itself to a point beyond the outer tip of the soft cannula. The needle 58 hereby prepares the way for the soft cannula 49 during the insertion process. The septum is made from a usual flexible polymer material. It is apparent from the foregoing description that the septum is only penetrated once by the insertion needle.

The means as shown for securing the cannula are provided in case the cannula is of a type which cannot be secured directly to the base element by e.g. gluing or welding. This is the case if the cannula is made from PTFE.

Figure 27:
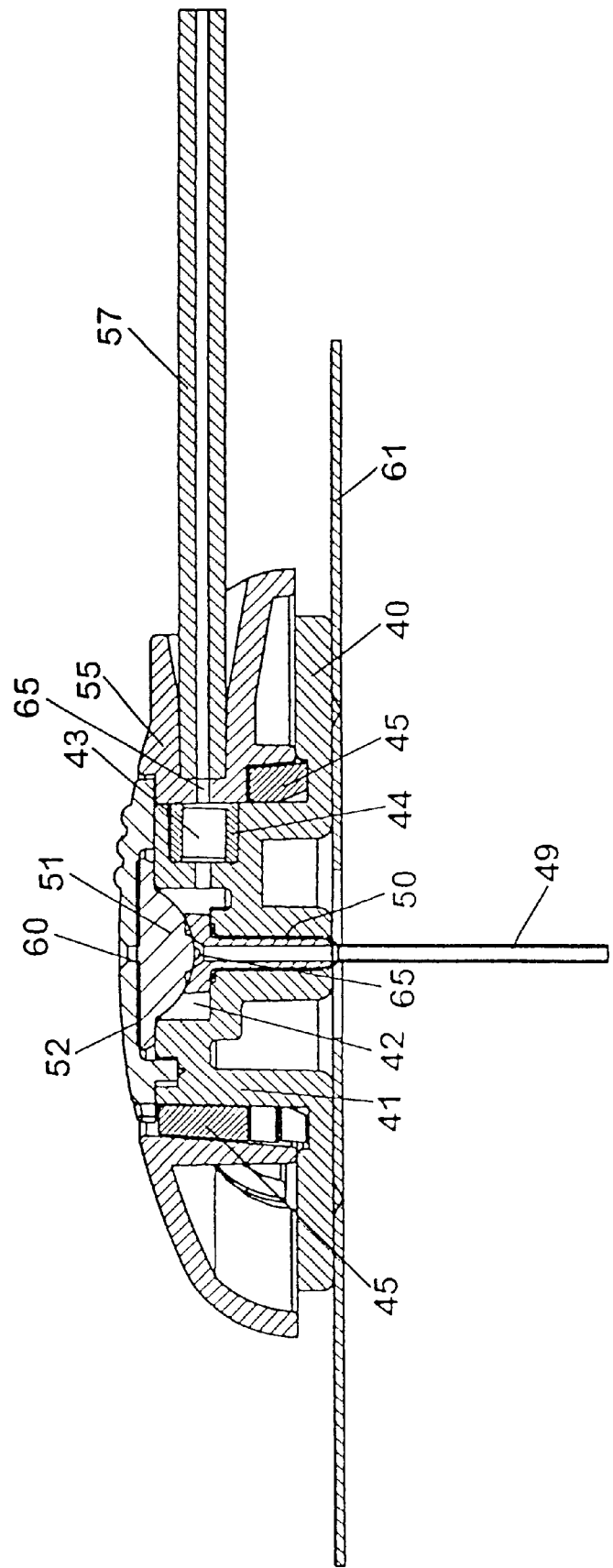
FIG. 27 is a sectional view taken along the line 27—27 in FIG. 25.

From FIG. 27 the infusion set appears in a state where the insertion needle has been removed. The medication can now be delivered through the cavity and through a slit in the holding means for the cannula to the cannula itself and further to the subcutaneous layer of the patient.

Figure 28:
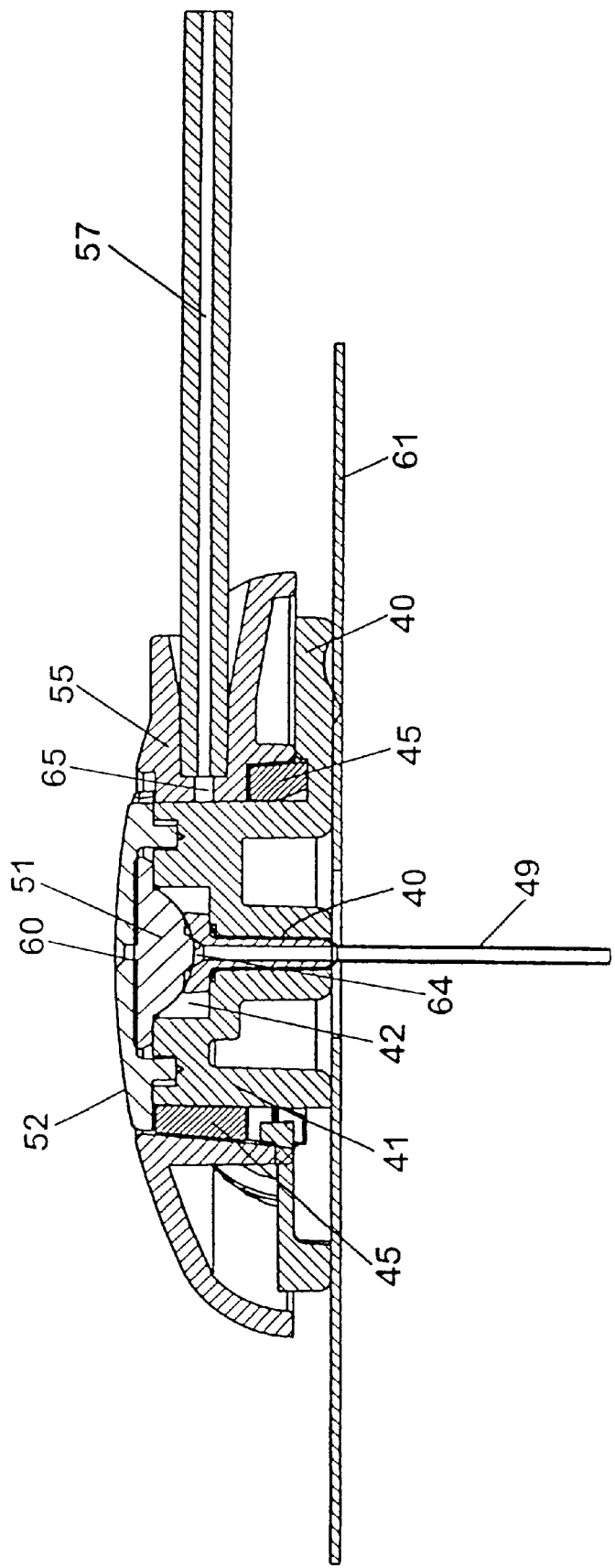
FIG. 28 is a sectional view taken along the line 28—28 in FIG. 23.

From FIG. 28 the infusion set appears in a state where the connector has been rotated to a release position. The bore 65 in the connector is now no longer aligned with the aperture 43 in the hub, which is close by the inwardly facing side of the closing element.

Figure 29:
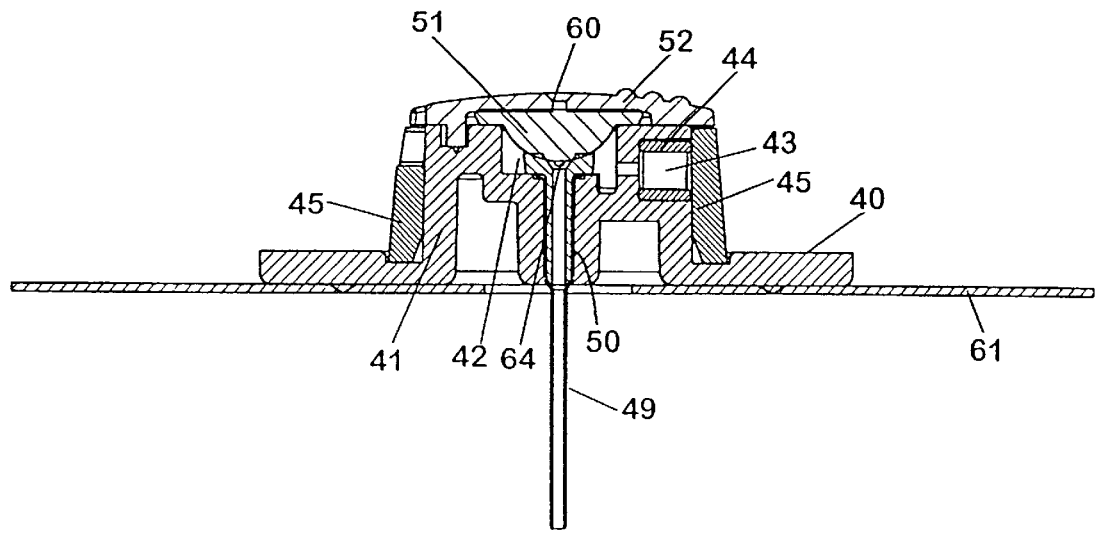
FIG. 29 is a sectional view taken along the line 29—29 in FIG. 24.
Figure 30:
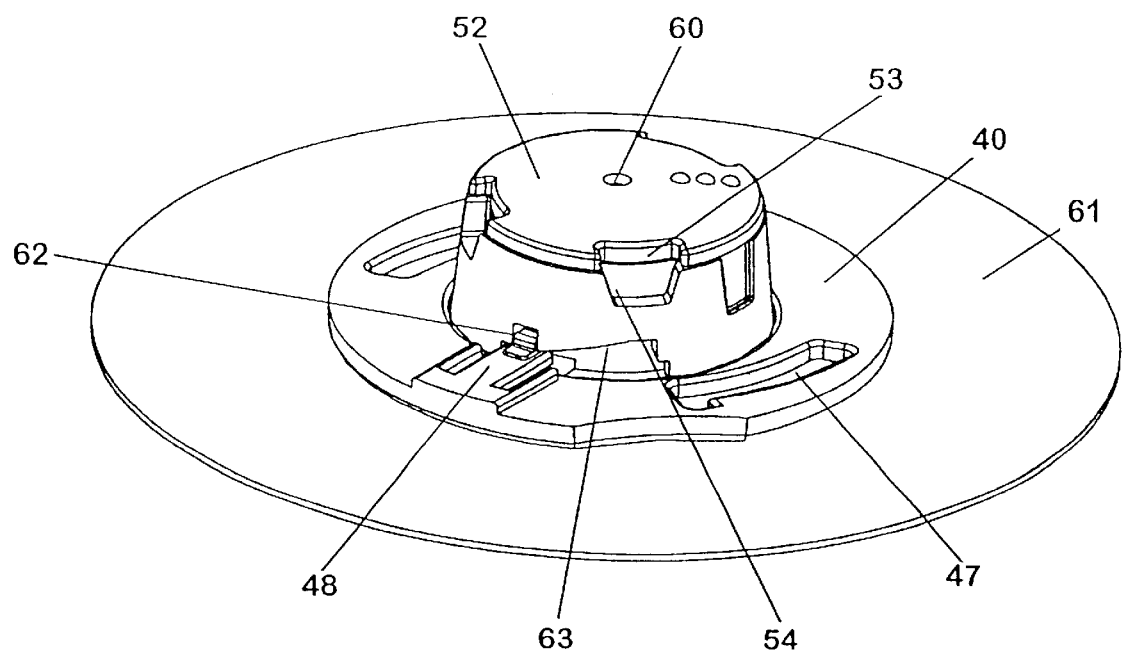
FIG. 30 is a perspective view of an infusion set corresponding to FIG. 24 where the connector means has been removed and where the closing element is in a locked position.
Figure 31:
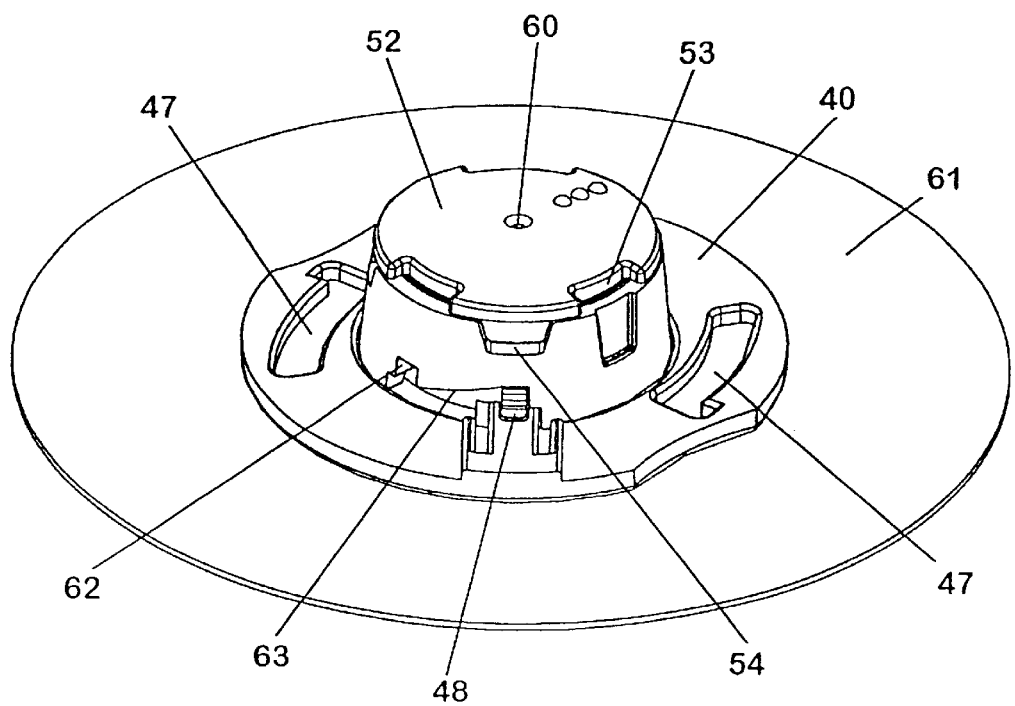
FIG. 31 is a perspective view of an infusion set corresponding to FIG. 30 where the connector means has been removed and where the closing element by activation of the locking means has been rotated to an open position.

From FIG. 29 the close abutment of the inwardly facing side on the closing element and the sealing means 44 appears As already mentioned the closing element 45 is mounted to be rotatable in relation to the base element 40. The closing element 45 is rotatable about an axis which in this embodiment extends co-axially with the longitudinally axis of the insertion needle 58 and the cannula 49. The rotation can take place between two extreme positions, namely a first position where the connector means 55 is secured in relation to the closing element and the base element as shown in FIG. 22, and a second position where the connector means 55 is releasable from the closing element 40 and the base element, as shown in FIG. 23. From FIG. 30 it appears that means for preventing unintended rotation of the closing element in relation to the base element are provided. These means comprise a biasing element 48 on the base part which in the unloaded state and upon an attempt to rotate the closing element will abut on the side of an arcute cut-out 62 in the closing element. Such rotation will lead to an opening of the infusion site which could cause a contamination. The release of the closing element 45 which can normally only be effected by mounting the connector 55 and rotating this is shown in FIG. 31 without the connector. Having pressed down the biasing element 48 to a position below the cut-out 62 and having rotated the closing element by means of the connector, the biasing element is relaxed at the end of an inclined cut-out 63 next to the arcuate cut-out 62.

Figure 32:
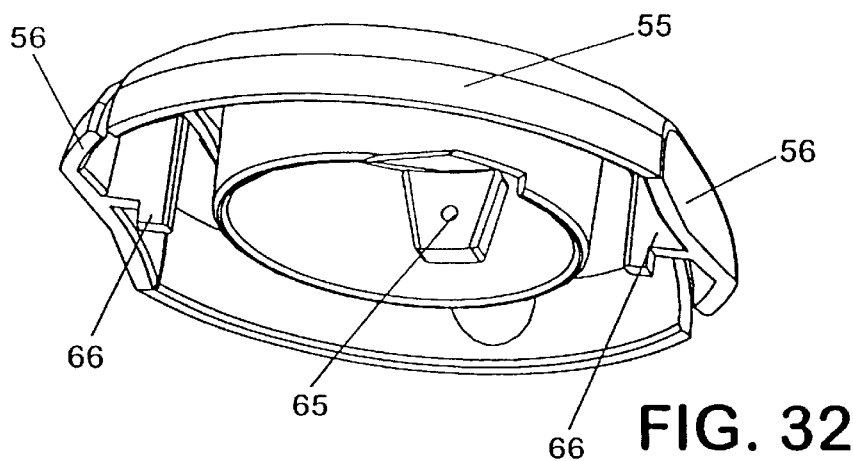
FIG. 32 is a bottom perspective view of a connector of an infusion set.
Figure 33:
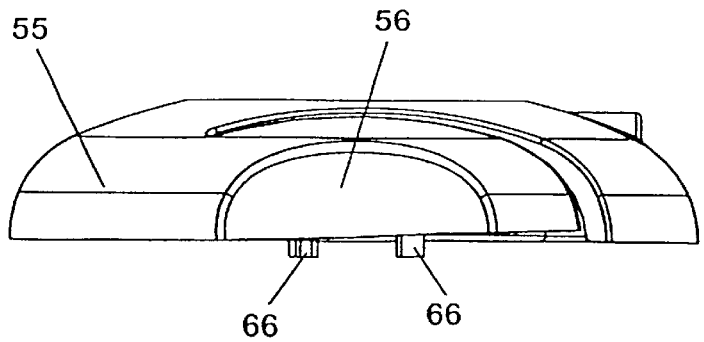
FIG. 33 is a side view of the connector shown in FIG. 32.

From FIG. 32 and FIG. 33 the connector appears. The bore 65 through which the medication is delivered appears as well as downwardly protruding taps 66 on the gripping elements 56. The taps 66 co-operate with the path 47 in the base part. These paths have the shape of a part circle having a centre displaced from the centre of rotation of the connector. Upon rotation of the connector, the taps will be forced in an inward direction until the end of the path is reached where this has an angled shape. Here the gripping arms and the taps will relax in a locked state of the connector in relation to the base part thereby preventing the connector from unintended release during use, which could lead to a harmfull condition for the user.

What is claimed is:

1. A subcutaneous infusion set comprising:
   a base element having a cavity, an entry lumen, a top side and a bottom side;
   a cannula mounted in said base element and extending from said bottom side of said base element, said cannula having a lumen therethrough, said lumen communicating with the entry lumen through said cavity;
   connector means for administering a fluid to said entry lumen;
   a closing element mounted on said base element to be rotatable about an axis through said base element and having an aperture, where the aperture in one position of the closing element in relation to the base element is aligned with said entry lumen of said base element and in a further rotated position of the closing element in relation to the base element the closing element covers said entry lumen in said base element.

2. An infusion set as defined in claim 1, wherein the base element comprises a hub with a top and a bottom and an outer surface extending between said top and said bottom, wherein the cavity is formed within said hub and said entry lumen extend between said outer surface and said cavity and wherein the closing element has substantially the form of a ring element.

3. An infusion set as defined in claim 2, wherein said connector means is secured in relation to said base element and where said closing element further comprises a flange, in the area around the aperture, thereby providing a pressure against said connector means upon rotation of said closing element.

4. An infusion set as defined in claim 2, wherein said cannula is a soft cannula, wherein said cavity extends to the top of said hub and wherein self-sealing means covering said cavity towards said top of said hub are provided, wherein an insertion needle is provided for removable insertion through an opening in said closing element, through said self-sealing means and through said cavity and said lumen of said soft cannula and extending beyond the length of said soft cannula.

5. An infusion set as defined in claim 1, wherein the connector means comprises an abutment area cooperating with said closing element in the area of the aperture.

6. An infusion set as defined in claim 1, wherein the connector means comprises a protruding part co-operating with an outer surface of said closing element and where means are provided for urging the connector means against said outer surface of said closing element.

7. An infusion set as defined in claim 6, wherein said closing element further comprise an inwardly facing surface directed towards the axis through said hub and wherein said connector means for administering fluid to said opening in said closing element comprise an outwardly facing surface directed away from said axis through said hub, said outwardly facing surface matching said inwardly facing surface of said closing element upon rotation of said closing element in relation to said base element.

8. A subcutaneous infusion set as defined in claim 7, wherein said inwardly facing surface has a curvature urging the connector means for administering medication towards the closing element.

9. An infusion set as defined in claim 1, further comprising sealing means between said base element and said closing element.

10. An infusion set as defined in claim 1, further comprising sealing means between said closing element and said connector means for administering a fluid.

11. A subcutaneous infusion set as defined in claim 1, further comprising means for releasably interlocking the base element and the connector means for administering a fluid in relation to a mutual rotation about said axis.

12. A subcutaneous infusion set as defined in claim 1, further comprising means for preventing a rotation of the closing element in relation to the base element when the connector means for administering medication to said aperture in said closing element is not present.

13. A subcutaneous infusion set as defined in claim 12, wherein said means for preventing a rotation comprises a biasing element forming part of the closing element or the base element.

14. An infusion set as defined in claim 1, wherein means for securing said base element in relation to the skin of a patient are provided.

15. An infusion part for use in a subcutaneous infusion set as defined in claim 1, the infusion part comprising:

a base element having a cavity, an entry lumen, a top side and a bottom side;

a cannula mounted in said base element and extending from said bottom side of said base element, said cannula having a lumen therethrough, said lumen communicating with the entry lumen through said cavity;

a closing element mounted on said base element to be rotatable about an axis through said base element and having an aperture, where the aperture in one position of the closing element in relation to the base element is aligned with said entry lumen of said base element and in further rotated position of the closing element in relation to the base element the closing element covers said entry lumen in said base element.

16. An infusion part as defined in claim 15, wherein the base element comprises a hub with a top and a bottom and an outer surface extending between said top and said bottom, wherein the cavity is formed within said cavity and said entry lumen extend between said outer surface and said cavity and wherein the closing element has substantially the form of a ring element.

17. An infusion part as defined in claim 15, further comprising sealing means between said base element and said closing element.

18. An infusion part as defined in claim 15, wherein means for securing said base element in relation to the skin of a patient are provided.

* * * * *